(12) United States Patent
Viswanathan et al.

(10) Patent No.: US 10,640,475 B2
(45) Date of Patent: *May 5, 2020

(54) COMPOSITIONS AND METHODS TO PRODUCE ALKOXYLATED TRIAZINE-ARLHYDROXY-ALDEHYDE CONDENSATES

(71) Applicant: Hexion Inc., Columbus, OH (US)

(72) Inventors: Ganapathy S. Viswanathan, Louisville, KY (US); Anthony Maiorana, Louisville, KY (US); Stephan Schröter, Essen (DE); Pravin Kukkala, Louisville, KY (US)

(73) Assignee: HEXION INC., Columbus, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/043,707

(22) Filed: Jul. 24, 2018

(65) Prior Publication Data

US 2019/0092736 A1    Mar. 28, 2019

Related U.S. Application Data

(63) Continuation-in-part of application No. 15/713,577, filed on Sep. 22, 2017, now Pat. No. 10,118,905.

(51) Int. Cl.
| | | |
|---|---|---|
| C07D 251/64 | (2006.01) |
| C08G 18/38 | (2006.01) |
| C08G 18/54 | (2006.01) |
| C08G 18/16 | (2006.01) |
| C08G 18/42 | (2006.01) |
| C08G 18/48 | (2006.01) |
| C08G 18/18 | (2006.01) |
| C08G 18/40 | (2006.01) |
| C08G 18/09 | (2006.01) |
| C08G 18/76 | (2006.01) |
| C07D 251/48 | (2006.01) |
| C08G 18/66 | (2006.01) |
| C08G 18/22 | (2006.01) |
| C07D 317/38 | (2006.01) |
| C07D 251/18 | (2006.01) |
| C08G 101/00 | (2006.01) |

(52) U.S. Cl.
CPC ......... *C07D 251/64* (2013.01); *C07D 251/18* (2013.01); *C07D 251/48* (2013.01); *C07D 317/38* (2013.01); *C08G 18/092* (2013.01); *C08G 18/163* (2013.01); *C08G 18/1808* (2013.01); *C08G 18/225* (2013.01); *C08G 18/3851* (2013.01); *C08G 18/4018* (2013.01); *C08G 18/4027* (2013.01); *C08G 18/4208* (2013.01); *C08G 18/4829* (2013.01); *C08G 18/544* (2013.01); *C08G 18/546* (2013.01); *C08G 18/6633* (2013.01); *C08G 18/6666* (2013.01); *C08G 18/7664* (2013.01); *C08G 2101/005* (2013.01); *C08G 2101/0008* (2013.01); *C08G 2101/0016* (2013.01); *C08G 2101/0025* (2013.01); *C08G 2105/02* (2013.01); *C08G 2170/20* (2013.01); *C08G 2350/00* (2013.01); *C08G 2410/00* (2013.01)

(58) Field of Classification Search
CPC .................................................. C07D 251/64
See application file for complete search history.

(56) References Cited

U.S. PATENT DOCUMENTS

| | | |
|---|---|---|
| 2,448,767 A | 9/1948 | Carlson |
| 2,987,555 A | 6/1961 | Davis |
| 3,265,668 A | 8/1966 | Dowbenko et al. |
| 3,328,321 A | 6/1967 | Wismer et al. |
| 3,399,151 A | 8/1968 | Kaiser |
| 3,470,118 A | 9/1969 | Forster |
| 3,497,465 A | 2/1970 | Kujawa et al. |
| 3,806,508 A * | 4/1974 | Weinrotter ........... C07D 251/18 544/196 |
| 4,032,514 A | 6/1977 | Buriks et al. |
| 4,060,501 A | 11/1977 | Naylor et al. |
| 4,067,843 A | 1/1978 | Annis et al. |
| 4,087,480 A | 5/1978 | Takahashi et al. |
| 4,107,229 A | 8/1978 | Tideswell et al. |
| 4,261,922 A | 4/1981 | Kem |
| 4,310,707 A | 1/1982 | Strege |
| 4,419,477 A | 12/1983 | Saeki et al. |
| 4,474,951 A | 10/1984 | Pope |
| 4,483,941 A | 11/1984 | Yang |
| 4,500,655 A | 2/1985 | Brennan |
| 4,680,054 A | 7/1987 | TakeMatsu et al. |
| 5,059,670 A | 10/1991 | Harris |
| 5,059,723 A | 10/1991 | Dressler |
| 5,104,987 A | 4/1992 | King |
| 5,272,226 A | 12/1993 | Lancaster et al. |
| 5,457,140 A | 10/1995 | Nunez et al. |
| 5,605,757 A | 2/1997 | Klett |
| 5,679,871 A | 10/1997 | Nava |
| 5,686,379 A | 11/1997 | Imanaka et al. |
| 6,229,054 B1 | 5/2001 | Dai et al. |
| 6,392,003 B1 * | 5/2002 | Kiuchi ................... C08G 14/10 428/524 |
| 6,498,278 B1 | 12/2002 | Clements et al. |

(Continued)

FOREIGN PATENT DOCUMENTS

| | | |
|---|---|---|
| CN | 105199069 A * | 12/2015 |
| CN | 107474070 A * | 12/2017 |

(Continued)

OTHER PUBLICATIONS

H-S Moon et al., 124 Journal of the American Chemical Society (2002) (Year: 2002).*

(Continued)

*Primary Examiner* — Alexander R Pagano

(57) ABSTRACT

The embodiments described herein generally relate to methods and chemical compositions of triazine-arylhydroxy-aldehyde condensates. In one embodiment, a triazine-arylhydroxy-aldehyde condensate is reacted with at alkoxylation agent to form alkoxylated triazine-arylhydroxy-aldehyde condensates.

20 Claims, No Drawings

(56) References Cited

U.S. PATENT DOCUMENTS

| | | | |
|---|---|---|---|
| 6,586,607 | B1 | 7/2003 | Durairaj et al. |
| 6,605,354 | B1 | 8/2003 | Gerber |
| 6,818,726 | B2 | 11/2004 | Ratzsch et al. |
| 7,767,778 | B2 | 8/2010 | Rawlins et al. |
| 9,133,377 | B2 | 9/2015 | Bremont et al. |
| 9,228,040 | B2 | 1/2016 | Pinto et al. |
| 9,249,251 | B2 * | 2/2016 | Viswanathan ......... C08G 14/10 |
| 10,118,905 | B1 * | 11/2018 | Viswanathan ....... C07D 251/64 |
| 10,435,503 | B2 * | 10/2019 | Viswanathan ......... C08G 18/73 |
| 2003/0045667 | A1 | 3/2003 | Ratzsch et al. |
| 2005/0192422 | A1 | 9/2005 | Da Costa et al. |
| 2007/0048522 | A1 | 3/2007 | Ratzsch et al. |
| 2012/0009407 | A1 | 1/2012 | Peeler et al. |
| 2012/0046424 | A1 * | 2/2012 | Viswanathan ......... C08G 14/10 525/480 |
| 2016/0010823 | A1 | 1/2016 | Seyrlehner et al. |
| 2016/0108231 | A1 | 4/2016 | Aube et al. |
| 2016/0168306 | A1 * | 6/2016 | Viswanathan ......... C08G 14/10 |
| 2017/0306077 | A1 | 10/2017 | Chaffanjon et al. |
| 2019/0092894 | A1 * | 3/2019 | Viswanathan ..... C08G 18/3851 |
| 2019/0092897 | A1 * | 3/2019 | Viswanathan ......... C08G 18/73 |

FOREIGN PATENT DOCUMENTS

| | | |
|---|---|---|
| EP | 0212214 | 3/1987 |
| GB | 758249 | 10/1956 |
| GB | 775459 | 5/1957 |
| GB | 934629 | 8/1963 |
| GB | 1029033 | 5/1966 |
| GB | 2350616 | 12/2000 |
| JP | 2008063453 | 3/2008 |
| JP | 2013041942 A * | 2/2013 |
| WO | WO2011/029711 | 3/2001 |
| WO | WO 2003/020512 | 3/2003 |
| WO | WO2012/016803 | 2/2012 |
| WO | WO2015/104048 | 7/2015 |
| WO | WO2017/160362 | 9/2017 |

OTHER PUBLICATIONS

A.M. Prokhorov et al., 24 Progress in Heterocyclic Chemistry (2012) (Year: 2012).*

English-language Machine Translation of JP 5750009 B (2015) (Year: 2015).*

English-language Machine Translation of CN 107474070 (2017) (Year: 2017).*

English-language Machine Translation of CN105199069 (2013) (Year: 2013).*

Borkovec, A. et al., Derivaties of Melamine, Entomology Research Div., US Dept. of Agriculture, Insent Chemosterilants vol. 10 pp. 457-461, Maryland, May 1967.

* cited by examiner

COMPOSITIONS AND METHODS TO PRODUCE ALKOXYLATED TRIAZINE-ARLHYDROXY-ALDEHYDE CONDENSATES

FIELD OF THE INVENTION

This invention relates to alkoxylated triazine-arylhydroxy-aldehyde condensate compositions and methods for making these compositions.

BACKGROUND OF THE INVENTION

Polyurethanes are one of the most versatile class of polymeric materials. They are particularly useful in rigid and flexible foams. Flexible polyurethane foams are used as cushioning for a variety of consumer and commercial products, including bedding, furniture, automotive interiors, carpet underlay and packaging. Rigid polyurethane and polyisocyanurate (polyiso) foams create one of the world's most popular, energy-efficient and versatile insulations. Environmental health and safety, along with fire protection, are driving change within the insulation industry. The high thermal insulation of rigid polyurethane makes them the most suited and efficient technologies to address these needs. These global trends drives demand for continuous innovation across the polyurethane industry.

Polyurethane foams are produced by reacting an isocyanate with a polyol. The polyol component is typically one or more polyols along with a surfactant, catalyst, fire retardant and a blowing agent to make a foam. The most common polyols used in the industry are polyether polyols and polyester polyols. Each of these class of compounds have their own merits and demerits. Polyether polyols provides hydrolytic stability, lower viscosity and flexibility. Aromatic polyester are known to contribute to flame retardance and higher modulus. However, they are typically limited in functionality and inherently, higher in viscosity and hence formulations especially in rigid PU systems have to use a co-polyol such as polyether polyols with higher functionality. Furthermore, sugar-based polyols that are one of the most commonly used co-polyol in these formulations do not offer any burn resistance.

Alkoxylated phenol-aldehyde resins have been found to be useful in the preparation of various polymeric products including polyurethane compositions and foamed products. These are typically called novolac based polyether polyols. They are prepared by reacting novolacs with alkylene oxides. These types of polyols have the advantage of having a high aromatic content which is known in the industry to aid in improved reaction to fire and can have high functionality. However, formulators still need to use other polyols along with amine-based catalysts and fire retardants to achieve the desired thermal, fire and mechanical performance.

The Spray Polyurethane Foam (SPF) market, for example, is one of the fastest growing polyurethane segments due to the superior ability of SPF to provide high insulation, reduce noise and for the ability to retrofit existing buildings and infrastructure. However, many SPF formulations utilize small molecule organic and inorganic catalysts to provide quick reaction and phosphate or phosphate-chlorinated additives in order to function and meet building regulations for fire ratings. Small molecule catalysts such as amines can be volatilized during spray polyurethane installation that poses health hazard. Small molecule fire retardants that are invariably added to these formulations, are under regulatory scrutiny for concerns related to their effect on the environment.

Thus, there is an increasing demand for better performing rigid polyurethane foams that have particular flammability specifications and acceptable physical properties. There exists a need in the industry for a polyol with high reactivity towards isocyanate, inherent flame resistance, high functionality to achieve the desired properties and to allow reduction or elimination of the volatile amine-based catalysts and small molecule flame retardants.

SUMMARY OF THE INVENTION

In one broad embodiment of the present invention, there is disclosed an alkoxylated triazine-arylhydroxy-aldehyde condensate compound. The compound is prepared by a process comprising, consisting of, or consisting essentially of: reacting a triazine-arylhydroxy-aldehyde condensate; and at least one an alkoxylation agent, optionally in the presence of a catalyst, to form an alkoxylated triazine-arylhydroxy-aldehyde condensate compound. The alkoxylation agent may be an alkylene oxide, alone or in combination with an alkylene carbonate. In a further embodiment, the alkoxylation agent may be an alkylene carbonate.

In one embodiment of the invention, a condensation product is provided including a reaction mixture comprising a triazine-arylhydroxy-aldehyde condensate, and an alkoxylation agent comprising an alkylene oxide and an optional alkylene carbonate, and an optional catalyst.

In another embodiment of the invention, an alkoxylated triazine-arylhydroxy-aldehyde condensate compound is provided.

In another embodiment of the invention, a process is provided including reacting a triazine-arylhydroxy-aldehyde condensate and at least one alkylene oxide, alone or in combination with an alkylene carbonate, optionally in the presence of a catalyst and forming an alkoxylated triazine-arylhydroxy-aldehyde condensate composition. In one embodiment, the condensate composition is free of a catalyst, free of a fire retardant, free of Mannich polyols, or combinations thereof. In one embodiment, the condensate composition is free of amine catalysts.

In another embodiment of the invention, a polymer is provided including using a formulation comprising a polyisocyanate and an isocyanate-reactive compound comprising at least one alkoxylated triazine-arylhydroxy-aldehyde condensate. An article may be prepared from the polymer. In one embodiment, the formulation is free of a catalyst, free of a fire retardant, free of Mannich polyols, or combinations thereof. In one embodiment, the formulation is free of amine catalysts.

In another embodiment of the invention, a process is provided including forming a reaction mixture comprising a polyisocyanate and an isocyanate-reactive compound comprising at least one alkoxylated triazine-arylhydroxy-aldehyde condensate, and curing the reaction mixture to form a polymer. In one embodiment, the reaction mixture is free of a catalyst, free of a fire retardant, free of Mannich polyols, or combinations thereof. In one embodiment, the formulation is free of amine catalysts. The process may further include applying the polymer to a substrate.

DETAILED DESCRIPTION OF THE INVENTION

Embodiments of the invention are directed to alkoxylated triazine-arylhydroxy-aldehyde condensates, methods for making the alkoxylated triazine-arylhydroxy-aldehyde condensates, and the use of alkoxylated triazine-arylhydroxy-aldehyde condensates in the manufacture of polyurethane and polyisocyanurate resins.

An alkoxylated triazine-arylhydroxy-aldehyde condensate is formed by reacting a triazine-arylhydroxy-aldehyde condensate with an alkylene oxide. Alternatively, An alkoxylated triazine-arylhydroxy-aldehyde condensate is formed by reacting a triazine-arylhydroxy-aldehyde condensate with an alkylene oxide and an alkylene carbonate. In a further alternative, An alkoxylated triazine-arylhydroxy-aldehyde condensate is formed by reacting a triazine-arylhydroxy-aldehyde condensate with an alkylene carbonate.

Any suitable triazine-arylhydroxy-aldehyde condensate can be used in the reaction with the alkylene oxide, the alkylene carbonate, or both. In various embodiments, the triazine-arylhydroxy-aldehyde condensate is formed from a reaction mixture of a triazine monomer, an arylhydroxy monomer, and an aldehyde monomer. In various embodiments, the triazine-arylhydroxy-aldehyde condensate is a novolac.

The triazine monomer can be a triazine compound or a triazine derivative. An example of a triazine compound is melamine and an example of a triazine derivative is a melamine derivative.

Suitable compounds that can be used as the triazine monomer include compounds from the aminotriazine group such as, 4-methyl-1,3,5-triazine-2-amine, 2-amino-4,6-dimethyl-1,3,5-triazine, melamine, hexamethoxymethylmelamine, hexamethylolmelamine, guanamine, acetoguanamine, propioguanamine, butyroguanamine, benzoguanamine, vinylguanamine, 6-(hydroxyphenyl)-2,4-diamino-1,3,5-triazine, and combinations thereof.

The arylhydroxy monomer can be any suitable aromatic monomer with one or more hydroxyl groups per molecule, such as a monohydroxy, dihydroxy or a trihydroxy benzene. They can be mononuclear or binuclear. In various embodiments, the arylhydroxy monomer is a phenol monomer compound. Phenol monomer compounds having at least one ortho or para position available for bonding are preferred compounds. The phenol monomer compound can be an unsubstituted or substituted compound, for example, with an alkyl group, a phenyl group, a hydroxybenzene group, an alkoxy group, and combinations and subsets thereof. The phenol monomer compound can also include compounds having up to about 15 carbon atoms such as up to about 8 carbon atoms. Examples of such arylhydroxy monomers include, but are not limited to phenol, cresols, xylenols, resorcinol, catechol, hydroquinone, naphthols, dihydroxynaphthalenes, biphenols, bisphenols, phloroglucinol, pyrogallol or their derivatives.

The aldehyde monomer includes compounds having one or more aldehyde functional groups (—CHO) and any compounds yielding aldehydes. The aldehyde monomer can be represented by the formula R—CHO, and R can be an aliphatic or aromatic organic functional group. The aldehyde monomer can be a dialdehyde such as glyoxal. Suitable aldehydes include, but are not limited to compounds such as formaldehyde, paraformaldehyde, acetaldehyde, i-butyraldehyde (isobutyraldehyde), benzaldehyde, acrolein, crotonaldehyde, salicylaldehyde, 4-hydroxybenzaldehyde, furfural, pyrrole-2-carboxaldehyde, cinnamaldehyde, trioxymethylene, paraldehyde, terephthaldialdehyde, glyoxal, glutaraldehyde and combinations thereof.

The triazine-arylhydroxy-aldehyde condensate can be comprised of a variety of triazine, arylhydroxy, and aldehyde combinations. In various embodiments, the condensate is a melamine, phenol, and formaldehyde novolac. Further details about the triazine-arylhydroxy-aldehyde condensate and its preparation can be found in U.S. Pat. Nos. 6,239,248 and 9,249,251, which are both herein incorporated by reference.

The triazine-arylhydroxy-aldehyde condensate is reacted with at least one alkoxylation agent to form the alkoxylated triazine-arylhydroxy-aldehyde condensate. The alkoxylation agent may be alkylene oxide, alone or in combination with an alkylene carbonate. Alternatively, the alkoxylation agent may be alkylene carbonate.

Suitable alkylene oxides may comprise linear aliphatic alkylene oxides, branched aliphatic alkylene oxides, cyclic aliphatic alkylene oxides, aromatic alkylene oxides, alkyl aromatic alkylene oxides, alkylene oxides with ethers (commonly known as glycidyl ethers), and alkylene oxides with esters (commonly known as glycidyl esters).

Examples of suitable alkylene oxides can be one or more alkylene oxides selected from the group comprising ethylene oxide, propylene oxide, glycidol, styrene oxide, epichlorohydrin, butylene oxide, isobutyleneoxide, cyclohexane oxide, 2,3-epoxyhexane, allyl glycidyl ether, methyl glycidyl ether, butyl glycidyl sulfide, glycidyl methyl sulfone, glycidyl methacrylate, glycidyl allyl phthalate, and combinations thereof. Examples of preferred alkylene oxides include compounds selected from the group consisting of ethylene oxide, propylene oxide, butylene oxide, and combinations thereof.

The alkylene oxide can comprise from about 5 wt. % to about 90 wt. % of the triazine-arylhydroxy-aldehyde condensate and at least one alkylene oxide reaction mixture. Alternatively, in one embodiment, the triazine-arylhydroxy-aldehyde condensate and alkoxylation agent may be present with a reactive site to alkoxylation agent ratio, such as alkylene oxide and/or alkylene carbonate, from about 20:1 to about 1:20.

If present, suitable alkylene carbonates may comprise linear aliphatic alkylene carbonates, branched aliphatic alkylene carbonates, aromatic alkylene carbonates, alkyl aromatic alkylene carbonates, alkyl hydroxide carbonates, vinyl carbonates, acrylic carbonates, and ester carbonates. Examples of preferred alkylene carbonates may include one or more alkylene carbonate selected from the group comprising ethylene carbonate, propylene carbonate, butylene carbonate, glycerol carbonate, styrene carbonate, 1-chloropropylene carbonate, isobutylene carbonate cyclohexene carbonate, allyl carbonate, methacrylate carbonate, vinyl carbonate, allyl phthalate carbonate, and combinations thereof. Examples of preferred alkylene carbonates include compounds selected from the group consisting of ethylene carbonate, propylene carbonate, butylene carbonate, and combinations thereof.

Suitable alkylene carbonate can be prepared from suitable mono-epoxide compounds such as ethylene oxide, propylene oxide, glycidol, styrene oxide, epichlorohydrin, butylene oxide, isobutyleneoxide, cyclohexane oxide, 2,3-epoxyhexane, allyl glycidyl ether, methyl glycidyl ether, butyl glycidyl sulfide, glycidyl methyl sulfone, glycidyl methacrylate, glycidyl allyl phthalate.

The alkylene carbonate can comprise from about 5 wt. % to about 50 wt. % of the triazine-arylhydroxy-aldehyde condensate and at least one alkylene carbonate, and optionally, at least one alkylene oxide, reaction mixture. Alternatively, the triazine-arylhydroxy-aldehyde condensate and at least one alkylene carbonate may be present with an reactive site to alkylene carbonate ratio from about 1:1 to about 1:2. In one embodiment, the alkoxylation agent can be one or more compounds selected from the group consisting of ethylene oxide, propylene oxide, butylene oxide, ethylene carbonate, propylene carbonate and mixtures thereof.

If both the alkylene oxide and the alkylene carbonate are present, the components can comprise from about 2 wt. % to about 90 wt. % of the triazine-arylhydroxy-aldehyde condensate, at least one alkylene oxide, and at least one alkylene carbonate, reaction mixture. Alternatively, the triazine-arylhydroxy-aldehyde condensate and the combined components of the at least one alkylene oxide and at least one alkylene carbonate may be present at reactive site to alkylene oxide and at least one alkylene carbonate ratio from about 20:1 to about 1:20.

In a further alternative embodiment, the alkylene carbonate can comprise from about 5 wt. % to about 90 wt. % of the triazine-arylhydroxy-aldehyde condensate and an alkylene carbonate reaction mixture.

A reactive site is defined as any site that has a labile proton below a pKa of 40 such as a phenolic hydroxyl, primary hydroxyl, secondary hydroxyl, tertiary hydroxyl, aminic hydroxyls such as primary amines, secondary amines, primary aromatic amines, or secondary aromatic amines. A primary amine would possess two reactive sites and a secondary amine would possess one reactive sites.

The triazine-arylhydroxy-aldehyde condensate is reacted with at least one alkylene oxide to form an alkoxylated triazine-arylhydroxy-aldehyde condensate. In various embodiments, reaction conditions can include a reaction temperature in the range of from about 50° C. to about 270° C. Any and all temperatures within the range of about 50° C. to about 270° C. are incorporated herein and disclosed herein; for example, the reaction temperature can be from about 100° C. to about 200° C., from about 140° C. to about 180° C., or from about 160° C. to about 175° C. The reaction conditions can also include a reaction pressure in the range of from about 0.01 bar to about 100 bar. Any and all pressures within the range of from 0.01 bar to 100 bar are included herein and disclosed herein; for example, the reaction pressure can be from about 0.1 bar to about 50 bar, from about 0.5 bar to about 20 bar, or from about 1 bar to about 10 bar.

The components can be added together in any suitable manner. For example, the reaction can take place in a batch system, a continuous system, a semi-batch system, or a semi-continuous system.

In various embodiments, the alkylene oxide can be added slowly to molten triazine-arylhydroxy-aldehyde condensate and then reacted until the alkylene oxide has been consumed. In various embodiments, the alkylene oxide can be bulk charged to a molten triazine-arylhydroxy-aldehyde condensate under pressure and reacted to a specific lowering of pressure or until all the alkylene oxide has been consumed.

The process of the invention may be conducted in a suitable solvent. Suitable solvents are those that dissolve the reactants and the product and are themselves inert in the process. After the reaction, such solvents can be removed from the reaction mixture through a distillation process. Examples of solvents include, but are not limited to acetone, methyl ethyl ketone, dioxane, tetrahydrofuran, and combinations thereof. In other embodiments, the alkoxylation of triazine-arylhydroxy-aldehyde condensate can be carried out in the presence of reactive diluents. Example of reactive diluents that can be used include, but are not limited to ethylene glycol, glycerol, methanol, ethanol, propanol, butanol, and combinations thereof. Alkylene oxide can be reacted with both the reactive diluent and the triazine-arylhydroxy-aldehyde condensate to yield liquid materials of various viscosities.

Optionally, the reaction between the triazine-arylhydroxy-aldehyde condensate and the alkylene oxide can take place in the presence of a catalyst. Suitable catalysts include metal hydroxides, metal carbonates, metal phosphates, tertiary amines, phosphines, transition metal bases, organic acids, inorganic acids, and combinations thereof. Examples of catalysts that can be used include, but are not limited to sodium hydroxide, potassium hydroxide, lithium hydroxide, ammonium hydroxide, magnesium hydroxide, calcium hydroxide, barium hydroxide, sodium carbonate, sodium bicarbonate, potassium carbonate, potassium bicarbonate, potassium phosphate, sodium phosphate, lithium phosphate, and combinations thereof. Examples of organic acids include oxalic acid, formic acid, acetic acid, trifluoroacetic acid, methane sulfonic acid, salicylic acid, benzoic acid, adipic acid, or p-toluenesulfonic acid; and examples of inorganic acids include hydrochloric acid, sulfuric acid, phosphoric acid, and combinations thereof. The organic acids and inorganic acids can also be used to neutralize the reaction mixture.

In one embodiment, the formulation used to form the condensate is free of a catalyst, free of a fire retardant, free of Mannich polyols, or combinations thereof. In one embodiment, the condensate is free of amine catalysts.

An organic acid such as oxalic acid, formic acid, acetic acid, trifluoroacetic acid, methane sulfonic acid, salicylic acid, phosphoric acid, benzoic acid, adipic acid, or p-toluenesulfonic acid can be used to neutralize the reaction mixture. If present, the catalyst may comprise from about 0.05 wt. % to about 5 wt. % of the triazine-arylhydroxy-aldehyde condensate and at least one alkylene oxide reaction mixture.

In various embodiments, the alkoxylated triazine-arylhydroxy-aldehyde condensate compound can be represented by Formula I below.

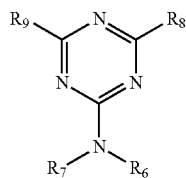

Formula I

The $R_6$ functional group is represented by Formula II or Formula III. The $R_7$ functional group of Formula I can be a hydrogen atom or represented by Formula II or Formula IV.

$R_8$ and $R_9$ can each independently be a hydrogen atom, an alkyl group with 1 to 10 carbon atoms, a vinyl group, a phenyl group, a hydroxyphenyl group, —NH(Formula IV), —N(Formula IV)$_2$, —NH(Formula II), —N(Formula II) (Formula IV), —N(Formula I)$_2$, —NH(Formula III), —N(Formula III)(Formula IV), —N(Formula III)$_2$, NH(Formula V), —N(Formula IV)(Formula V), —N(Formula V)$_2$, or —NH$_2$.

The structures of Formulas II, III, IV, and V are depicted below.

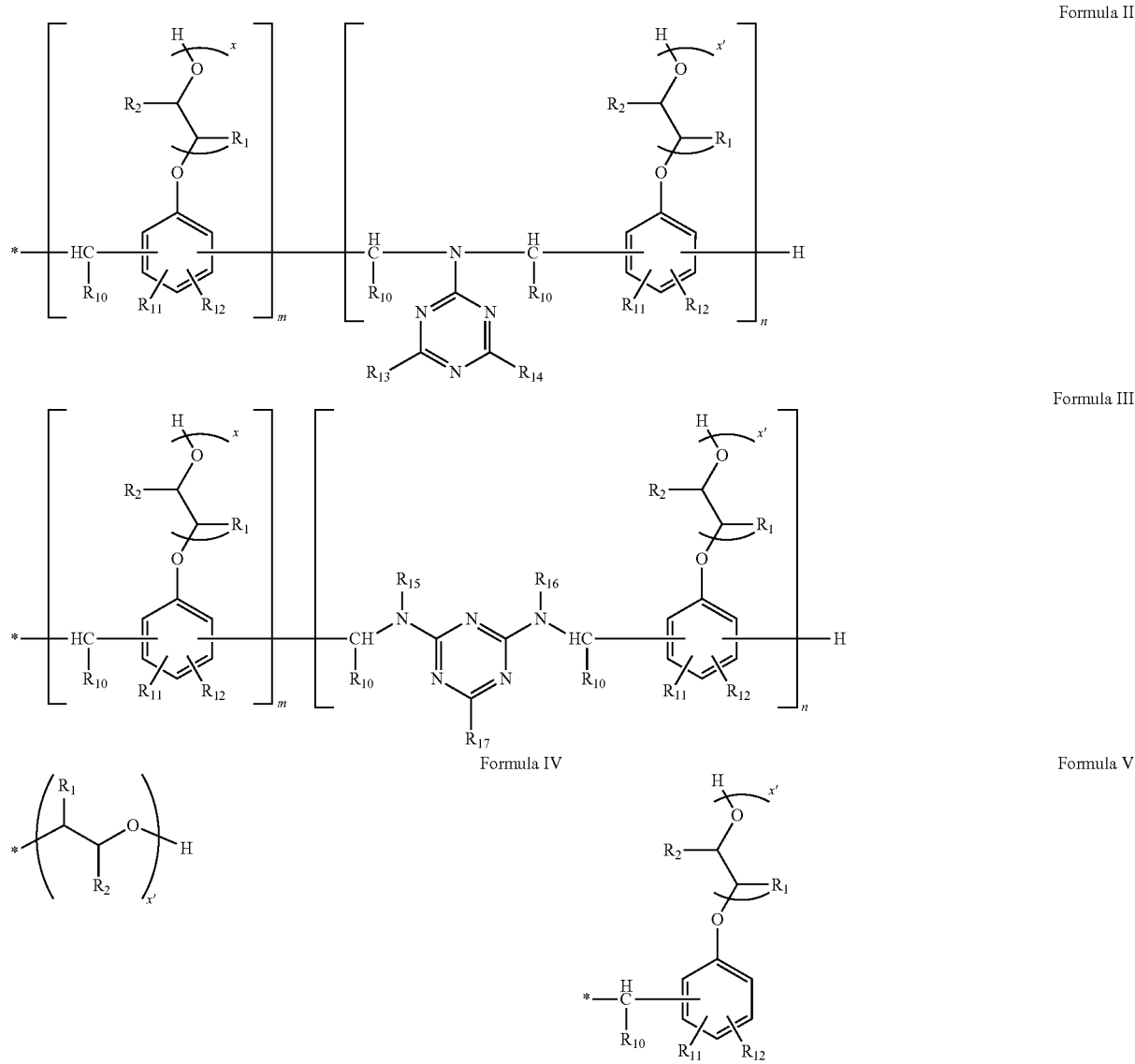

Formula II

Formula III

Formula IV

Formula V

In the above Formulas, $R_1$ and $R_2$ are independently a hydrogen atom, an alkyl group having 1 to 4 carbon atoms, a vinyl group, or an alkyl group with 1 to 4 carbon atoms containing a hydroxyl group.

$R_{10}$ can be a hydrogen atom, an alkyl group with 1 to 10 carbon atoms, an alkyl group with 1 to 10 carbon atoms containing a hydroxyl group, a phenyl group, a vinyl group, a propenyl group, a hydroxyl-containing phenyl group, a pyrrole group, or a furanyl group.

$R_{11}$ and $R_{12}$ are each independently a hydrogen atom, an alkyl group with 1 to 10 carbon atoms, an alkoxy group having 1 to 10 carbon atoms, a phenyl group, a hydoxybenzene group, or an alkyl group with 1 to 10 carbon atoms with at least one carbon substituted with i) a hydroxyl group, ii) a hydroxybenzene group or iii) a phenyl group. In various embodiments, $R_{11}$ and $R_{12}$ can jointly form a common aromatic ring with or without a hydroxyl group.

$R_{13}$ and $R_{14}$ are each independently a hydrogen atom, an alkyl group with 1 to 10 carbon atoms, a vinyl group, a phenyl group, a hydroxyphenyl group, —NH(Formula IV), —N(Formula IV)$_2$, —NH(Formula IV), —N((Formula II)(Formula IV)), —N(Formula IV)$_2$, or —NH$_2$.

$R_{15}$, $R_{16}$, and $R_{17}$ are each independently a hydrogen atom, an alkyl group with 1 to 10 carbon atoms, a vinyl group, a phenyl group, a hydroxyphenyl group, —NH(Formula IV), —N(Formula IV)$_2$, —NH(Formula V), —N(Formula IV)(Formula V), —N(Formula V)$_2$, or —NH$_2$.

In the Formulas above, each m is independently from 1 to 10, each n is independently from 0 to 10, each x is independently from 3 to 10, and each x' is independently from 3 to 10 when alkylene carbonates are used as the sole alkoxylating agent. Monomers depicted by m and n can be arranged in any order, combination, or sub-combination.

In the Formulas above, each m is independently from 1 to 10, each n is independently from 0 to 10, each x is independently from 1 to 20, and each x' is independently from 1 to 20 when alkylene oxides are the sole alkoxylation agent. Monomers depicted by m and n can be arranged in any order, combination, or sub-combination. In another embodiment, each x is independently from 1 to 2, and each x' is independently from 1 to 2 when alkylene oxides are the sole alkoxylation agent. In another embodiment, each x is independently from 3 to 20, and each x' is independently from 3 to 20 when alkylene oxides are fed to the reaction mixture to produce block-copolymer structures and alkylene oxides are the sole alkoxylation agent. Monomers depicted by m and n can be arranged in any order, combination, or subcombination.

In the Formulas above, each m is independently from 1 to 10, each n is independently from 0 to 10, each x is independently from 1 to 20, and each x' is independently from 1 to 20 when alkylene oxides and alkylene carbonates are both used as alkoxylation agents. Monomers depicted by m and n can be arranged in any order, combination, or subcombination. In another embodiment, each x is independently from 1 to 2, and each x' is independently from 1 to 2 when alkylene oxides and alkylene carbonates are both used as alkoxylation agents. In another embodiment, each x is independently from 3 to 20, and each x' is independently from 3 to 20 when alkylene carbonates and alkylene oxides are used as alkoxylation agents. In another embodiment, the average of all x and x' is greater than 2 when the average of all x and x' is greater than 2 when the alkoxylation agent is a combination of an alkylene oxide and an alkylene carbonate.

The alkoxylated triazine-arylhydroxy-aldehyde condensates generally have a nitrogen content of from about 0.5 wt. % (weight percent) to about 41 wt %, such as from about 1 wt. % to about 23 wt. %, for example, from about 5 wt. % to about 15 wt. %, in various other embodiments.

The alkoxylated triazine-arylhydroxy-aldehyde condensates generally have an aromatic content of from about 0.5 wt. % (weight percent) to about 69 wt %, such as from about 5 wt. % to about 40 wt. %, for example, from about 12 wt. % to about 30 wt. %, in various other embodiments.

Examples of the alkoxylated triazine-arylhydroxy-aldehyde condensate are represented by Formulas VIa-VIh, below:

Formula VIa

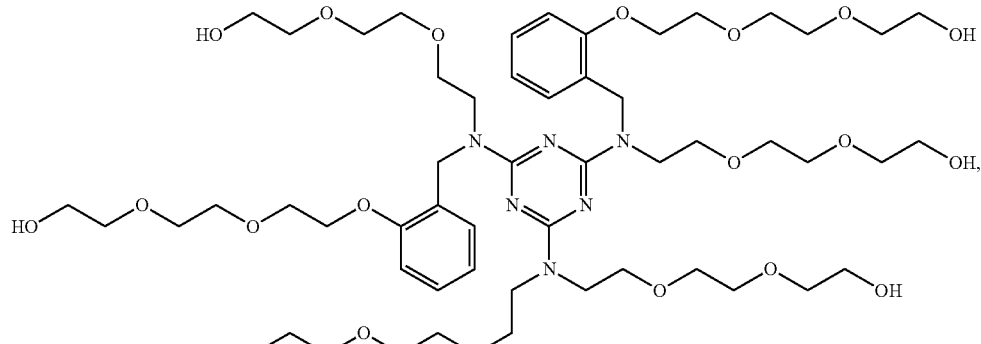

Formula VIb

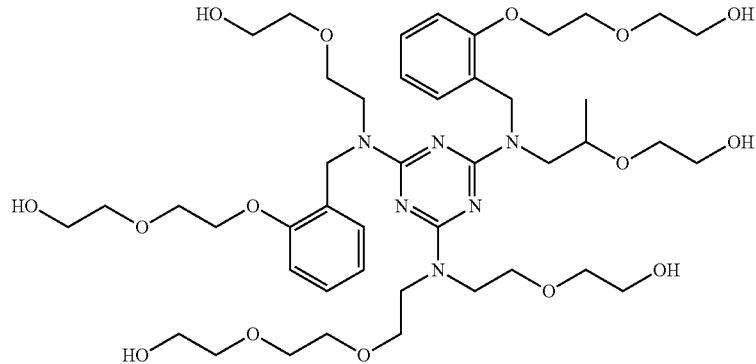

Formula VIc

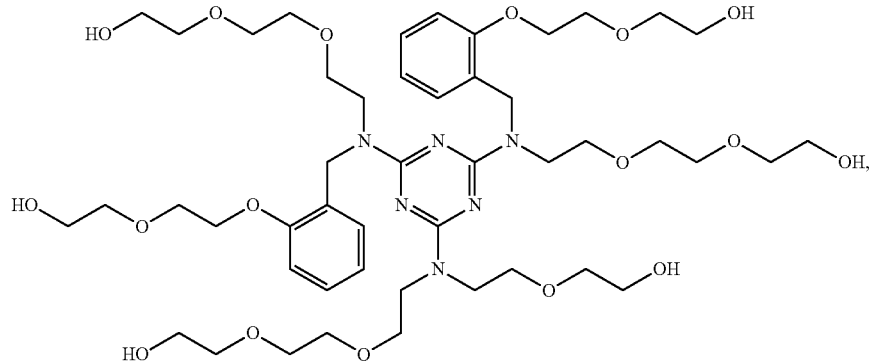

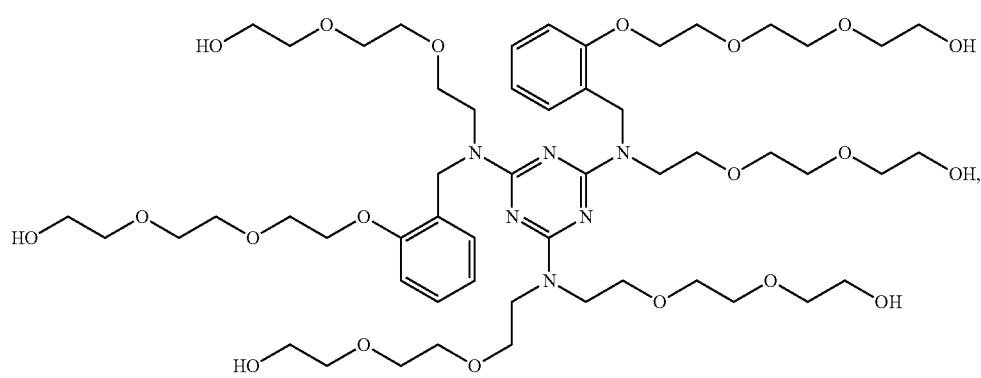
Formula VId
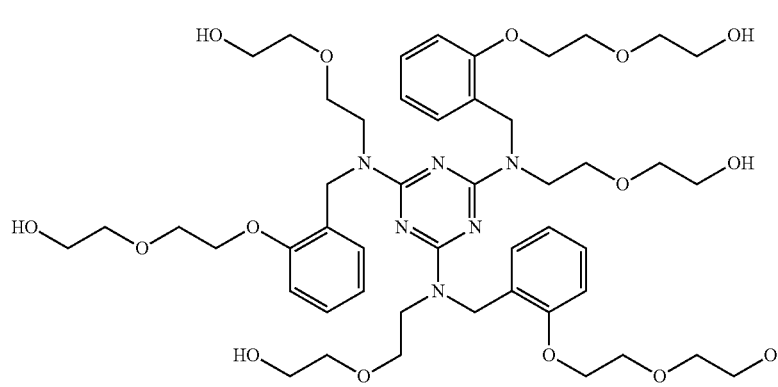
Formula VIe
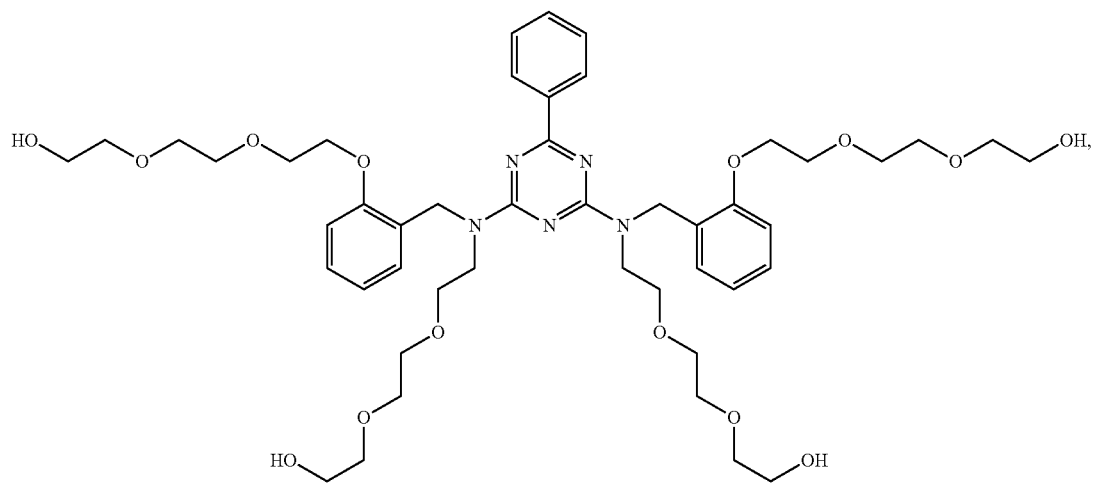
Formula VIf
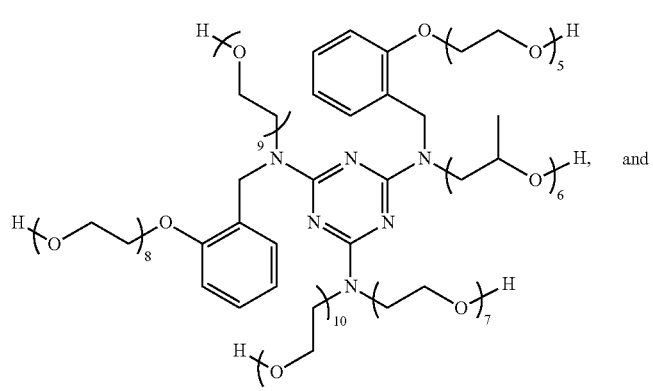
Formula VIg
and

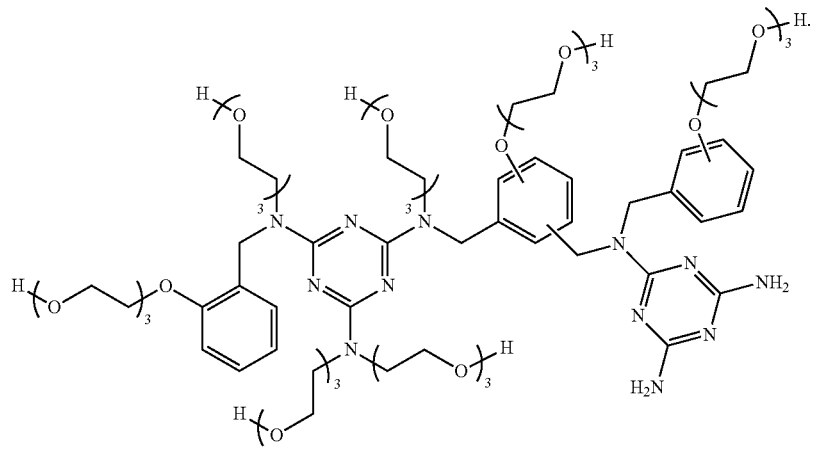

Formula VIh

The alkoxylated triazine-arylhydroxy-aldehyde condensates of this invention generally have a viscosity from about 0.01 Pascal second to 60 Pascal seconds at 25° C., such as from about 0.01 Pascal second to 30 Pascal seconds at 25° C. Any and all ranges within 0.01 to 60 Pascal seconds are included herein and disclosed herein, for example, the alkoxylated triazine-arylhydroxy-aldehyde condensates in solvents can have a viscosity in the range of from 0.1 to 30 Pascal seconds or from 10 to 20 Pascal seconds at 25° C. The alkoxylated triazine-arylhydroxy-aldehyde condensates of this invention can additionally exhibit non-newtonian behavior such as shear thinning behavior, which can be influenced by the type of alkoxylating agent and the number of x and x' introduced via the alkoxylating agent.

The manufacturing of the triazine-arylhydroxy-aldehyde condensate and forming the alkoxylated triazine-arylhydroxy-aldehyde condensate composition can be carried out in the same reactor or different reactors. The manufacturing of triazine-arylhydroxy-aldehyde condensate and/or forming the alkoxylated triazine-arylhydroxy-aldehyde condensate composition may be carried out in a continuous, semi-continuous, semi-continuous to batch, or batch type process and/or reactor.

The alkoxylated triazine-arylhydroxy-aldehyde condensates of this invention can be used as polyisocyanate-reactive compounds to make polyurethanes and polyisocyanurate-based polymers.

In one embodiment, a polymer may be prepared using a formulation, referred to herein as a reaction mixture, comprising a polyisocyanate and an isocyanate-reactive compound comprising at least one alkoxylated triazine-arylhydroxy-aldehyde condensate as described herein. The polyisocyanate component may also be referred to as the "A Side" in a polyurethane reaction process. The isocyanate-reactive compound component, such as the alkoxylated triazine-arylhydroxy-aldehyde condensate described herein alone or in combination with another polyol, may also be referred to as the "B Side" in a polyurethane reaction process. In one embodiment, the formulation or reaction mixture is free of a catalyst, free of a fire retardant, free of Mannich polyols, or combinations thereof. In one embodiment, the formulation is free of amine catalysts.

The at least one polyisocyanate comprises from about 33 wt. to about 83 wt., such as from about 49 wt. to about 51 wt., of the reaction mixture, the isocyanate-reactive compound comprises from about 13 wt. to about 51 wt., such as from about 38 wt. to about 40 wt., of the reaction mixture, wherein the total amount of components equal 100 wt. % of the reaction mixture. The reaction mixture may further include optional additive materials as described herein, and if present, may be present in an amount from about 4 wt. to about 16 wt. %, such as from about 11 wt. to about 13 wt. %, of the formulation or reaction mixture, wherein the total amount of components equal 100 wt. % of the reaction mixture.

In various embodiments, a reaction mixture is formed with at least one polyisocyanate and at least one alkoxylated triazine-arylhydroxy-aldehyde condensate.

Suitable polyisocyanates include diisocyanates, triisocyanates, and combinations thereof. Examples of suitable polyisocyanates include, but are not limited to, m-phenylene diisocyanate, toluene-2,4-diisocyanate, toluene-2,6-diisocyanate, hexamethylene-1,6-diisocyanate, tetramethylene-1,4-diisocyanate, cyclohexane-1,4-diisocyanate, hexahydrotoluene diisocyanate, naphthylene-1,5-diisocyanate, methoxyphenyl-2,4-diisocyanate, diphenylmethane-4,4'-diisocyanate, diphenylmethane-2,4-diisocyanate, 4,4'-biphenylene diisocyanate, 3,3'-dimethoxy-4,4'-biphenyl diisocyanate, 3,3'-dimethyl-4,4'-biphenyl diisocyanate, 3,3'-dimethyldiphenylmethane-4,4'-diisocyanate, 4,4',4''-triphenyl methane triisocyanate, a polymethylene polyphenylisocyanate, polymeric diphenylmethane diisocyanate (PMDI), isophorone diisocyanate, toluene-2,4,6-triisocyanate, 4,4'-dimethyldiphenylmethane-2,2',5,5'-tetraisocyanate, isophorone diisocyanate, hexamethylene-1,6-diisocyanate, polymethylene polyphenylisocyanate, and combinations thereof. Diphenylmethane-4,4'-diisocyanate, diphenylmethane-2,4-diisocyanate and mixtures thereof are generically referred to as MDI and all can be used. Poly versions of the compounds are may also be used, such as polymeric diphenylmethane diisocyanate (PMDI). Toluene-2,4-diisocyanate, toluene-2,6-diisocyanate and mixtures thereof are generically referred to as TDI and all can be used.

Any of the foregoing polyisocyanates can be modified to include urethane, urea, biuret, carbodiimide, allophonate, uretonimine, isocyanurate, amide, or like linkages. Examples of modified isocyanates of these types include various urethane group and/or urea group-containing prepolymers and so-called 'liquid MDI' products and the like.

In various embodiments, the polyisocyanate can be a blocked isocyanate, where a standard polyisocyanate is prereacted with a blocking agent containing active hydrogen groups, which can then be deblocked at temperatures greater than 40° C. (typically in the range of from 100° C. to 190° C.). Examples of blocking agents include, but are not limited to γ-caprolactam, phenol, methyl ketone oxime, 1,2,4-triazole, dimethyl malonate, and combinations thereof.

The isocyanate-reactive compound comprising at least one alkoxylated triazine-arylhydroxy-aldehyde condensate may further include one or more additional polyols.

Polyols which can be used in conjunction with the alkoxylated triazine-arylhydroxy-aldehyde condensate include polyether polyols. These may be prepared by polymerizing an alkylene oxide onto an initiator compound that has multiple active hydrogen atoms. Suitable initiator compounds include, but are not limited to alkylene glycols, glycol ethers, glycerine, trimethylolpropane, sucrose, glucose, fructose, phenol formaldehyde condensates, ethylene diamine, hexamethylene diamine, diethanolamine, monoethanolamine, piperazine, aminoethylpiperazine, diisopropanolamine, monoisopropanolamine, methanol amine, dimethanol amine, and toluene diamine. An example of such a polyol is Poly-G 74-376, a sucrose initiated polyether polyol made with ethylene oxide and propylene oxide commercially available from Monument Chemical.

Polyester polyols can also be used as part of the isocyanate-reactive compound. Polyester polyols include reaction products of polyols, usually diols, with polycarboxylic acids or their anhydrides, usually dicarboxylic acids or dicarboxylic acid anhydrides. The polycarboxylic acids or anhydrides can be aliphatic, cycloaliphatic, aromatic, and/or heterocyclic. An example of such a polyol is Terol 250, an aromatic polyester polyol commercially available from Huntsman Corporation.

The isocyanate-reactive compounds may also include a Mannich polyol. The Mannich polyol most established in the formulations especially in the spray foam application is the reaction product of nonyl phenol, formaldehyde, and diethanolamine. Manufacturers of Mannich polyols provide formulation flexibility by varying the ratio of formaldehyde, ethanolamine, and alkoxylate to provide a specific functionality and equivalent weight. The Mannich polyol used as one of the reference polyols in the examples herein is one that is also nonyl phenol initiated. In another embodiment, the isocyanate-reactive compound may be free of Mannich polyols. An example of a Mannich polyol is Jeffol R-470X, commercially available from Huntsman Corporation.

In various embodiments, the alkoxylated triazine-arylhydroxy-aldehyde condensate is present in the isocyanate-reactive compound in a range of from about 1 weight percent to about 50 weight percent. Any and all ranges between 1 and 50 weight percent are included herein and disclosed herein; for example, the alkoxylated triazine-arylhydroxy-aldehyde condensate can be present in the isocyanate-reactive compound in a range of from 5 weight percent to 35 weight percent, from 15 weight percent to 25 weight percent, or from 9 weight percent to 21 weight percent.

In various embodiments, the alkoxylated triazine-arylhydroxy-aldehyde condensate has been observed to have a sufficiently high reactivity that a catalyst is optional. The reaction and/or reaction mixture of the alkoxylated triazine-arylhydroxy-aldehyde condensate and polyisocyanate compound may be free of a catalyst, such as free of an amine catalyst. Additionally, The reaction and/or reaction mixture of the alkoxylated triazine-arylhydroxy-aldehyde condensate and polyisocyanate compound may be free of a catalyst, free of a fire retardant, free of Mannich polyols, or combinations thereof.

In one embodiment, the polyisocyanate and alkoxylated triazine-arylhydroxy-aldehyde condensate mixture further comprises a phosphorus-containing flame retardant, a diluent, a catalyst, or combinations thereof. In one embodiment, the polyisocyanate and alkoxylated triazine-arylhydroxy-aldehyde condensate mixture further comprises a cell opener, a surfactant, a blowing agent, and combinations thereof.

In various embodiments, the alkoxylated triazine-arylhydroxyl-aldehyde condensate has been observed to have a sufficient reactivity that the addition of a catalyst is not needed for polymer forming reactions. The polyisocyanate and alkoxylated triazine-arylhydroxy-aldehyde condensate mixture may be may be free of a catalyst, free of a fire retardant, free of Mannich polyols, or combinations thereof. In one embodiment, the condensate mixture may be free of an amine catalyst.

Optionally, in various embodiments, the polyisocyanate and alkoxylated triazine-arylhydroxy-aldehyde condensate mixture can also include a catalyst. Examples of catalysts include, but are not limited to tertiary amines such as dimethylbenzylamine, 1,8-diaza(5,4,0)undecane-7, pentanrrethyldiethylenetriamine, dimethylcyclohexylamine, and triethylene diamine. Potassium salts such as potassium acetate and potassium octoate can also be used as catalysts. In various embodiments, the alkoxylated triazine-arylhydroxyl-aldehyde condensate through its inherent high reactivity towards isocyanate (autocatalytic), minimizes the use of a catalyst or allows the formulation to be free of a catalyst as described herein.

In various embodiments, the alkoxylated triazine-arylhydroxy-aldehyde condensate also contains a diluent. Suitable diluents include, but are not limited to polyglycols, etherified polyglycols, dibasic esters of acids, and combinations thereof. Examples of diluents include, but are not limited to, ethylene glycol, glycerol, diethylene glycol, monomethyl ether of ethylene glycol, dimethyl ether of ethylene glycol, diethyl adipate, dimethyl adipate, diethyl succinate, dimethyl succinate, and combinations thereof.

Depending upon the particular type of polymer being produced and the necessary attributes of the polymer, a wide variety of additional materials can be present during the reaction of the polyisocyanate compound with the alkoxylated triazine-arylhydroxy-aldehyde condensate. These additive materials include, but are not limited to, surfactants, blowing agents, cell openers, fillers, pigments and/or colorants, desiccants, reinforcing agents, biocides, preservatives, antioxidants, flame retardants, and combinations thereof. The additive materials may be present in an amount from about 0 wt. to about 20 wt. %, such as from about 4 wt. to about 16 wt. %, for example, from about 11 wt. to about 13 wt. %, of the formulation or reaction mixture.

If a flame retardant is included, the flame retardant is can be a phosphorus-containing flame retardant. Examples of phosphorus-containing flame retardants include, but are not limited to triethyl phosphate (TEP), triphenyl phosphate (TPP), trischloropropylphosphate (TCPP), dimethylpropanephosphate, resorcinol bis(diphenylphosphate) (RDP), bisphenol A diphenyl phosphate (BADP), and tricresyl phosphate (TCP), dimethyl methylphosphonate (DMMP), diphenyl cresyl phosphate and aluminium diethyl phosphinate.

The relative amounts of polyisocyanate and alkoxylated triazine-arylhydroxy-aldehyde condensate are selected to produce a polymer. The ratio of these components is generally referred to as the 'isocyanate index' which means 100 times the ratio of isocyanate groups to isocyanate-reactive groups provided by the alkoxylated triazine-arylhydroxy-aldehyde condensate. The isocyanate index is generally at least 50 and can be up to 1000 or more, for example from about 50 to about 900. Rigid polymers such as structural polyurethanes and rigid foams are typically made using an isocyanate index of from 90 to 200. When flexible or semi-flexible polymers are prepared, the isocyanate index is generally from 70 to 125. Polymers containing isocyanurate groups are often made at isocyanate indices of at least 150, up to 600 or more.

To form the polymer, the polyisocyanate compound and the alkoxylated triazine-arylhydroxy-aldehyde condensate are mixed and cured. The curing step is achieved by subjecting the reaction mixture to conditions sufficient to cause the polyisocyanate compound and alkoxylated triazine-arylhydroxy-aldehyde condensate to react to form the polymer.

An example would be mixing the the alkoxylated triazine-arylhydroxy-aldehyde condensate with pMDI for 10 seconds at ambient conditions in order to generate a reaction between the hydroxyl groups and the isocyanate. This reaction generates heat and depending on the length of alkoxylation can yield rigid or flexible foams.

A wide variety of polymers can be made in accordance with the invention through the proper selection of particular alkoxylated-triazine-arylhydroxy-aldehyde condensates, particular polyisocyanates, the presence of optional materials as described below, and reaction conditions. The process of the invention can be used to produce polyurethane and/or polyisocyanurate polymers of various types, including rigid polyurethane foams, sealants and adhesives (including moisture-curable types), hot-melt powders, wood binders, cast elastomers, flexible or semi-flexible reaction injection molded parts, rigid structural composites, flexible polyurethane foams, binders, cushion and/or unitary backings for carpet and other textiles, semi-flexible foams, pipe insulation, automotive cavity sealing, automotive noise and/or vibration dampening, microcellular foams such as shoe soles, tire fillers and the like. These polymers can then be used to manufacture articles.

The novel polymers produced herein may be applied to substrates as part of the polymer production process, such as point of use applications, or applied after complete polymer production for later use in application processes. Suitable substrates may include inorganic material, such as silica or metal, or an organic material, such as wood or plastic, or a combination thereof. Examples of suitable substrates include proppants and proppant substrates, wood, building materials, and structural surfaces, among others.

EXAMPLES

For the examples, the triazine-arylhydroxy-aldehyde condensate compositions were prepared using methods described in U.S. Pat. No. 9,249,251, which is incorporated herein by reference to the extent not inconsistent with the invention.

The following methods were utilized for Examples 1-6 for the data reported in Tables 1 and 2.

% Water:

The percentage of water remaining in the product after alkoxylation was determined by a standard Karl Fischer titration via a Karl Fischer titration apparatus which is similar to ASTM D6304.

Hydroxyl Value:

The value was obtained from utilizing the titration method as specified by American Oil Chemists' Society (AOCS) CD 13-60 method.

5% Solubility in Water:

The was determined by mixing 5 grams of the materials from examples 1-6 with 95 grams of distilled dionized water for 30 minutes and checking the visual appearance of the system. If the system was clear and exhibited no sediment it would be considered soluble and if the system exhibited any haze, cloudiness, or sediment it was considered insoluble.

Viscosity at 30° C.:

The viscosity of the materials were determined from a parallel plate Rheometer operated in rotational mode with a scanning shear rate of 0.1 to 100 l/s at 30° C. The viscosity of the materials of extrapolated to the zero shear viscosity and was reported in mPa·s.

pH (5% in IPA/Water):

The pH was determined by dissolving the material in 50% isopropanol (IPA) in water and utilizing a calibrated pH probe to read the pH of the overall system.

Control

A triazine-arylhydroxy-aldehyde condensate Control sample was prepared according to the process U.S. Pat. No. 9,249,251. It is briefly described in part as follows. 546.0 gram of phenol (5.8 moles), 1.1 g benzoic acid, and 79.1 g of melamine (0.63 moles) were charged to a reaction vessel to form a reaction mixture. The reaction mixture was heated to 80° C. and 55.8 g of formaldehyde was added in the form of a 50% solution in water over 40 minutes. The reaction was atmospherically distilled to 123° C. after addition and maintained at 123° C. for 2 hours. The reaction mixture was then cooled to 80° C. and 37.2 g of aqueous formaldehyde in the form of a 50% solution in water was added over 30 minutes and then atmospherically distilled to 123° C. and maintained at 123° C. for 2 hours. The reaction mixture was then further atmospherically distilled to 165° C. and then was gradually vacuumed distilled to 27 inches of mercury over 3 hours while maintaining 165° C. and then heated to 175° C. while maintaining 27 inches of mercury. The reaction mixture was held for 1 hour at 175° C. and then steam sparged for 60 minutes while under vacuum distillation. A total of 426.6 g of distillate was removed and 212.9 g of arylhydroxy-aldehyde condensate was discharged from the reaction vessel and upon cooling exhibited a brittle and solid like materials properties.

Example 1

500 grams of triazine-arylhydroxy-aldehyde condensate formed from the Control example and 50% potassium hydroxide in methanol was charged to a 2 L pressure reactor equipped with mechanical agitator, reflux condenser, thermocouple, and thermocouple controlled heating mantle. The reactor was flushed with nitrogen to remove air and heated to 90° C. followed by vacuum dehydration at 120° C. to remove trace water and methanol. The mixture was then heated to a temperature of 150-160° C. Then, 20% of 1015 grams of ethylene oxide was then charged to the flask to initiate the reaction followed by the addition of the remaining ethylene oxide to a pressure of 4.0 kg/cm$^2$. The reaction mixture was allowed to react at 165° C. at 4.0 kg/cm$^2$ then cooled to 70-75° C. and neutralized to a pH of 7-8. The yield was 87%

Example 2

500 grams of triazine-arylhydroxy-aldehyde condensate formed from the Control example and 50% potassium hydroxide in methanol was charged to a 3 L pressure reactor equipped with mechanical agitator, reflux condenser, thermocouple, and thermocouple controlled heating mantle. The reactor was flushed with nitrogen to remove air and heated to 90° C. followed by vacuum dehydration at 120° C. to remove trace water and methanol. The mixture was then heated to a temperature of 150-160° C. Then, 20% of 3254 grams of ethylene oxide was then charged to the flask to initiate the reaction followed by the addition of the remaining ethylene oxide to a pressure of 4.0 kg/cm². The reaction mixture was allowed to react at 165° C. at 4.0 kg/cm² then cooled to 70-75° C. and neutralized to a pH of 7-8. The yield was 85%

Example 3

135 grams of triazine-arylhydroxy-aldehyde condensate formed from the Control example and 50% potassium hydroxide in methanol was charged to a 2 L pressure reactor equipped with mechanical agitator, reflux condenser, thermocouple, and thermocouple controlled heating mantle. The reactor was flushed with nitrogen to remove air and heated to 90° C. followed by vacuum dehydration at 120° C. to remove trace water and methanol. The mixture was then heated to a temperature of 150-160° C. Then, 20% of 1370 grams of ethylene oxide was then charged to the flask to initiate the reaction followed by the addition of the remaining ethylene oxide to a pressure of 4.0 kg/cm². The reaction mixture was allowed to react at 165° C. at 4.0 kg/cm² then cooled to 70-75° C. and neutralized to a pH of 7-8. The yield was 92%.

The compositions of Examples 1-3 were tested for physical properties. Results are shown in Table 1: Physical Properties of Triazine-arylhydroxy-aldehyde condensates alkoxylated with Ethylene Oxide.

TABLE 1

| Parameters | Control | Example 1 | Example 2 | Example 3 |
|---|---|---|---|---|
| % Water | 0.1 | 0.5 | 0.1 | 0.2 |
| Hydroxyl value (mg KOH/g) | 739 | 368 | 209 | 158 |
| 5% solubility in water | Insoluble | Insoluble | Insoluble | Soluble & clear |
| Viscosity at 30° C. (mPa · s) | Solid | 13000 | 370 | 900 |
| pH (5% in IPA/Water) | 6.5 | 7.2 | 7.4 | 7.6 |

Table 1 demonstrates the properties of the alkoxylated triazine-arylhydroxy-aldehyde condensates after alkoxylation and shows a control prior to alkoxylation. The properties, specifically viscosity, hydroxyl value the % water, and the pH, are important for the application of alkoxylated triazine-arylhdroxy-aldehyde condensates in the preparation of polyurethane foams. The solubility in water indicates if the resulting alkoxylated triazine-arylhydroxy-aldehyde condensates were hydrophilic or hydrophobic. The Example 3 condensate being soluble in water and thus hydrophilic or miscible with water, and Example 1 and 2 condensates being insoluble and, thus, hydrophobic. These examples further indicate that increasing alkoxylation length with ethylene oxide corresponds to condensates being more hydrophilic thereby increasing the water solubility until a water soluble product is formed.

In addition, the alkoxylation yields materials that are liquid at 30° C. and enables their use into liquid polyurethane applications such as mixing with other polyols with addition of heat or require special handling conditions. Finally, the hydroxyl number for the control sample is extremely high at 739 mg KOH/g and would require a high amount of isocyanate to maintain a typical isocyanate index for polyurethane foams, whereas hydroxyl numbers in the range of 150-400 mg KOH/g are more suitable for most polyurethane foam applications.

Example 4

408 grams of triazine-arylhydroxy-aldehyde condensate formed from the Control example and 50% potassium hydroxide in methanol was charged to a 2 L pressure reactor equipped with mechanical agitator, reflux condenser, thermocouple, and thermocouple controlled heating mantle. The reactor was flushed with nitrogen to remove air and heated to 90° C. followed by vacuum dehydration at 120° C. to remove trace water and methanol. The mixture was then heated to a temperature of 150-160° C. Then, 20% of 1092 grams of propylene oxide was then charged to the flask to initiate the reaction followed by the addition of the remaining propylene oxide to a pressure of 4.0 kg/cm². The reaction mixture was allowed to react at 165° C. at 4.0 kg/cm² then cooled to 70-75° C. and neutralized to a pH of 7-8. The isolated yield was 48%

Example 5

185 grams of triazine-arylhydroxy-aldehyde condensate formed from the Control example and 50% potassium hydroxide in methanol was charged to a 2 L pressure reactor equipped with mechanical agitator, reflux condenser, thermocouple, and thermocouple controlled heating mantle. The reactor was flushed with nitrogen to remove air and heated to 90° C. followed by vacuum dehydration at 120° C. to remove trace water and methanol. The mixture was then heated to a temperature of 150-160° C. Then, 20% of 1316 grams of propylene oxide was then charged to the flask to initiate the reaction followed by the addition of the remaining propylene oxide to a pressure of 4.0 kg/cm². The reaction mixture was allowed to react at 165° C. at 4.0 kg/cm² then cooled to 70-75° C. and neutralized to a pH of 7-8. The isolated yield was 86%

Example 6

105 grams of triazine-arylhydroxy-aldehyde condensate formed from the Control example and 50% potassium hydroxide in methanol was charged to a 2 L pressure reactor equipped with mechanical agitator, reflux condenser, thermocouple, and thermocouple controlled heating mantle. The reactor was flushed with nitrogen to remove air and heated to 90° C. followed by vacuum dehydration at 120° C. to remove trace water and methanol. The mixture was then heated to a temperature of 150-160° C. Then, 20% of 1405 grams of propylene oxide was then charged to the flask to initiate the reaction followed by the addition of the remaining propylene oxide to a pressure of 4.0 kg/cm². The reaction mixture was allowed to react at 165° C. at 4.0 kg/cm² then cooled to 70-75° C. and neutralized to a pH of 7-8. The yield was 89%.

The compositions of Examples 4-6 were tested for physical properties. Results are shown in Table 2: Physical Properties of Triazine-arylhydroxy-aldehyde condensates alkoxylated with Propylene Oxide.

TABLE 2

| Parameters | Control | Example 4 | Example 5 | Example 6 |
|---|---|---|---|---|
| % Water | 0.1 | 0.2 | 0.3 | 0.4 |
| Hydroxyl value (mg KOH/g) | 739 | 240.2 | 210 | 180 |
| 5% solubility in water | Insoluble | Insoluble | Insoluble | Insoluble |
| Viscosity at 30° C. (cps) | Solid | 522 | 890 | 500 |
| pH (5% in IPA/Water) | 6.5 | 7.5 | 7.7 | 7.5 |

Table 2 demonstrates the properties of the alkoxylated triazine-arylhydroxy-aldehyde condensates after alkoxylation with propylene oxide and compares the results against a control of triazine-arylhydroxy aldehyde condensate. The properties are important for the application of alkoxylated triazine-arylhydroxy aldehyde condensates in the preparation of polyurethane foams, specifically viscosity, hydroxyl value the % water, and the pH. The solubility in water was used as an indication if the resulting alkoxylated triazine-arylhydroxy-aldehyde condensates were hydrophilic or hydrophobic and it can be seen that the the alkoxylated triazine-arylhydroxy-aldehyde condensates prepared with propylene oxide are all hydrophobic and not soluble in water even with long propoxylation lengths as seen in Example 6.

Example 7: Viscosities of Alkoxylated Triazine-Arylhydroxy-Aldehyde Condensates An ARES-G2 rheometer (TA Instruments) equipped with stainless steel parallel plates was operated under rotational mode to determine the viscosities of Examples 1-6 at 25° C., 30° C., 35° C., and 40° C. The viscosity was determined from a "zero-shear" approximation in which the viscosity is measured as a function of shear rate (0.1-100 i/s). The zero shear viscosity was determined by extrapolation of the viscosity curve to zero shear, which takes into account non-Newtonian behavior at low shear rates such as shear thinning. Due to the zero-shear approximation the viscosities appear to be higher than being reported within the Newtonian region of the viscosity curve. Ten data points were measured for every magnitude change of shear rate such as 10 points between 0.1 and 1 l/s. The lower temperature was determined when the materials exhibited non-Newtonian behavior such as shear thinning. Results are shown in Tables 3a-3b: Condensate Viscosity Results for Examples 1-6, below. Examples that exhibited shear thinning are denoted with (ST).

TABLE 3a

| Temperature (° C.) | Control | Viscosity Example 1 Condensate (Pa · s) | Viscosity Example 2 Condensate (Pa · s) | Viscosity Example 3 Condensate (Pa · s) |
|---|---|---|---|---|
| 25 | Solid | 22000 | 490 | 14000 (ST) |
| 30 | Solid | 13000 | 370 | 900 |
| 35 | Solid | 8000 | 280 | 540 |
| 40 | Solid | 5000 | 200 | 400 |

TABLE 3b

| Temperature (° C.) | Control | Viscosity Example 4 Condensate (Pa · s) | Viscosity Example 5 Condensate (Pa · s) | Viscosity Example 6 Condensate (Pa · s) |
|---|---|---|---|---|
| 25 | Solid | 734 | 1300 | 700 |
| 30 | Solid | 522 | 890 | 500 |
| 35 | Solid | 370 | 600 | 370 |
| 40 | Solid | 270 | 400 | 277 |

Tables 3a and 3b show the temperature dependence of viscosity for the different alkoxylated triazine-arylhydroxy-aldehyde condensates. Temperature has a significant influence on the viscosity of the products with a 5° C. change in temperature at times reducing the viscosity by 40% for Newtonian alkoxylated triazine-arylhydroxy-aldehyde condensates and 93% for the Non-Newtonian alkoxylated triazine-arylhydroxy-aldehyde condensates. The data is important for polyurethane formulators as viscosity of each component in a polyurethane system can have significant impacts on the overall properties of the final system.

Based upon the results of Tables 1-4, an alkoxylated triazine-arylhydroxy-aldehyde condensate can be used as a rheology modifier for polyurethane crosslinkers to further adjust the viscosities of polyurethane systems.

Example 8 (Polyurethane)

8.85 grams of the alkoxylated triazine-arylhydroxy-aldehyde condensate with an average repeat unit of 3 ethylene oxide units was mixed with 10 grams of pMDI for 20 seconds with a metal spatula. The mixture exhibited an exotherm within 20 seconds. The material exhibited slight foaming due to residual water, hardened, and was tack free after 30 seconds. The final material was a solid intractable material that was rigid and had a foam like structure.

Example 9

5.0 grams of the alkoxylated triazine-arylhydroxy-aldehyde condensate with an average repeat unit of 8 ethylene oxide units was mixed with 10 grams of pMDI for 10 seconds with a metal spatula. The mixture exhibited an exotherm within 10 seconds. The material exhibited a slight foaming due to residual water, hardened, and was tack free after 30 seconds. The final material was an intractable material that had some flexibility and a foam like structure.

Example 10

3.8 grams of the alkoxylated triazine-arylhydroxy-aldehyde condensate with an average repeat unit of 15 ethylene oxide units was mixed with 10 grams of pMDI for 10 seconds with a metal spatula. The mixture exhibited an exotherm within 15 seconds. The material exhibited a slight foaming due to residual water and was tack free after 30 seconds. The material was a flexible foam even when at room temperature.

Example 11

5 mg of sample was cut from the material produced from Example 9 and placed in a hermetically sealed differential scanning calorimetry pan. The sample was exposed to a heat/cool/heat cycle from −50 to 180° C. at 10° C./minute ramping rate and an uncontrolled crash cool to −50° C. on the cooling cycle. The first heating cycle demonstrated that the material exhibited impartial cure and had a peak exotherm temperature at 95° C. and a total heat of enthalpy of 23.7 J/g. The glass transition temperature from the first heating scan was 14° C. and on the second heating scan was 34° C.

Example 12

5 mg of sample was cut from the material produced from Example 10 and placed in a hermetically sealed differential scanning calorimetry pan. The sample was exposed to a heat/cool/heat cycle from −50 to 180° C. at 10° C./minute ramping rate and an uncontrolled crash cool to −50° C. on the cooling cycle. The first heating cycle demonstrated that the material exhibited full cure and exhibited no exothermal transitions. The glass transition temperatures from both heating scans were 9.8° C. and 10° C.

Example 13

5 mg of sample was cut from the material produced from Example 11 and placed in a hermetically sealed differential scanning calorimetry pan. The sample was exposed to a heat/cool/heat cycle from −80 to 180° C. at 10° C./minute ramping rate and an uncontrolled crash cool to −50° C. on the cooling cycle. The first heating cycle demonstrated that the material exhibited full cure and exhibited no exothermal transitions. The glass transition temperatures from both heating scans were −38° C. and −37° C.

Method for Thermogravimetric Analysis 10 mg of sample was cut from the material produced from Examples 9, 10, or 11 was placed in an alumina thermogravimetric analysis crucible and heated from room temperature to 1000° C. The onset of degradation was characterized by the weight loss of 5 ($T_{d5\%}$) and 10% ($T_{d10\%}$) and the peak degradation temperature, which was calculated from the derivative of the weight curve (%/° C.). The results are reported in Table 4: Thermogravimetric Analysis Results.

TABLE 4

| Length of Ethoxylation | Peak Degradation | $T_{d5\%}$ | $T_{d10\%}$ |
| --- | --- | --- | --- |
| Example 11 | 397 | 223 | 255 |
| Example 12 | 406 | 264 | 295 |
| Example 13 | 407 | 262 | 314 |

Table 4 indicates that the onset of degradation for the polyurethanes prepared from Examples 11, 12, and 13 exhibit different thermal stabilities. The onset of degradation was determined by the weight loss at 5% ($T_{d5\%}$) and 10% ($T_{d10\%}$). Example 13 exhibited the highest thermal stability with a $T_{d5\%}$ of 262° C. and $T_{d10\%}$ of 314° C. The polyurethanes from Example 13 exhibited about 6% higher thermal stability than example 12 and 18% higher thermal stability than example 11. This indicates that ethoxylation length plays an important role in the thermal stability of the final polyurethane polymer.

Method for Preparing Foams

Foams were prepared using a high-torque mixer (CRAFSTMAN 10-Inch Drill Press, Model No. 137.219000) at 3,100 rpm speed. Polyol components and isocyanate components of the foam systems were mixed for 5 seconds. Afterwards, the mixture was transferred into an open cake box before the cream time and was allowed to rise. Foams were prepared by pouring the foaming mix into cake boxes of 9"×9"×5" dimensions. The foams were used to assess cream time, gel time, rise time, tack-free time, density, and visual appearance of cell structure.

For Examples 14-20, Lupranate M20S is a polymeric methylene diphenyl diisocyanate (pMDI) available from BASF Corporation.

Example 14

A polyurethane foam was prepared, according to the process herein, by reacting Lupranate M20S, a polymeric methylene diphenyl diisocyanate with an isocyanate index of 110, (A side) and a polyol component (B side) prepared from the corresponding components in Table 5. The mix time was held constant and the cream time, gel time, rise time, and tack free time, were all measured after the mixture had been poured into a polyethylene lined cardboard box. The resulting foam had a density of 29.52 kilogram per cubic meter and had a uniform and coarse cell structure.

Example 15

A polyurethane foam was prepared, according to the process herein, by reacting Lupranate M20S, a polymeric methylene diphenyl diisocyanate with an isocyanate index of 110, (A side) and a polyol component (B side) prepared from the corresponding components in Table 5. The mix time was held constant and the cream time, gel time, rise time, and tack free time, were all measured after the mixture had been poured into a polyethylene lined cardboard box. The resulting foam had a density of 30.69 kilogram per cubic meter and had a uniform and fine cell structure.

Example 16

A polyurethane foam was prepared, according to the process herein, by reacting Lupranate M20S, a polymeric methylene diphenyl diisocyanate with an isocyanate index of 110, (A side) and a polyol component (B side) prepared from the corresponding components in Table 5. The mix time was held constant and the cream time, gel time, rise time, and tack free time, were all measured after the mixture had been poured into a polyethylene lined cardboard box. The resulting foam had a density of 28.45 kilogram per cubic meter and had a uniform and slightly coarse cell structure.

Example 17

A polyurethane foam was prepared, according to the process herein, by reacting Lupranate M20S, a polymeric methylene diphenyl diisocyanate with an isocyanate index of 110, (A side) and a polyol component (B side) prepared from the corresponding components in Table 5. The mix time was held constant and the cream time, gel time, rise time, and tack free time, were all measured after the mixture had been poured into a polyethylene lined cardboard box. The resulting foam had a density of 30.23 kilogram per cubic meter and had a uniform and fine cell structure.

Example 18

A polyurethane foam was prepared, according to the process herein, by reacting Lupranate M20S, a polymeric methylene diphenyl diisocyanate with an isocyanate index of 110, (A side) and a polyol component (B side) prepared from the corresponding components in Table 5. The mix time was held constant and the cream time, gel time, rise time, and tack free time, were all measured after the mixture had been poured into a polyethylene lined cardboard box. The resulting foam had a density of 37.25 kilogram per cubic meter and had a very fine cell structure.

Example 19

A polyurethane foam was prepared, according to the process herein, by reacting Lupranate M20S, a polymeric methylene diphenyl diisocyanate with an isocyanate index of 110, (A side) and a polyol component (B side) prepared from the corresponding components in Table 5. The mix time was held constant and the cream time, gel time, rise time, and tack free time, were all measured after the mixture had been poured into a polyethylene lined cardboard box. The resulting foam had a density of 28.90 kilogram per cubic meter and had a fine cell structure.

Example 20

A polyurethane foam was prepared, according to the process herein, by reacting Lupranate M20S, a polymeric methylene diphenyl diisocyanate with an isocyanate index of 110, (A side) and a polyol component (B side) prepared from the corresponding components in Table 5. Example 20 formulation is free of a catalyst. The mix time was held constant and the cream time, gel time, rise time, and tack free time, were all measured after the mixture had been poured into a polyethylene lined cardboard box. The resulting foam had a density of 42.36 kilogram per cubic meter.

commercially available from Invista, Inc. CO-28B is a cell opener commercially available from Ventrex Chemical. Dow Corning 193 is a silicone surfactant commercially available from Dow Corning. Solstice LBA is a hydrofluorinated olefin blowing agent commercially available from Honeywell Inc.

The alkoxylated triazine-arylhydroxy-aldehyde (ATAHA) condensate in Table 5 was prepared by the following procedure. 1000 grams of triazine-arylhydroxy-aldehyde condensate, 50 grams of glycerol, 6.6 grams of potassium hydroxide dissolved in 13.3 grams of methanol was charged to a 5 L pressure reactor equipped with mechanical agitator, reflux condenser, thermocouple, and thermocouple controlled heating mantle. The reactor was flushed with nitrogen to remove air and heated to 90° C. followed by vacuum dehydration at 120° C. to remove trace water and methanol. The mixture was then heated to a temperature of 140-150° C. Then, 59.25 grams of propylene oxide was charged to the vessel and allowed to react followed by heating the reaction mixture to a temperature of 155-160° C. Then, 2200 grams of ethylene oxide was added to a pressure of 3.5 to 4.0 kg/cm$^2$. After completion, the reaction mixture was then cooled to 70-75° C. and neutralized with 16 grams of salicylic acid. The yield was 95% and the material had a viscosity of 12400 mPa·s at 30° C., an OH # of 364 mg KOH/g, and a moisture content of 0.3%.

TABLE 5

| Component | Ex. 14 | Ex. 15 | Ex. 16 | Ex. 17 | Ex. 18 | Ex. 19 | Ex. 20 |
|---|---|---|---|---|---|---|---|
| Terol 250 | 46.11 | 46.11 | 46.11 | 46.11 | 46.11 | 46.11 | 46.11 |
| Jeffol R-470X | 30.74 | 0 | 15.37 | 15.37 | 0 | 10.25 | 0 |
| Poly-G 74-376 | 0 | 15.37 | 15.37 | 0 | 0 | 10.25 | 0 |
| ATAHA condensate | 0 | 15.37 | 0 | 15.37 | 30.74 | 10.25 | 30.74 |
| DBE Esters | 8.4 | 8.4 | 8.4 | 8.4 | 8.4 | 8.4 | 8.4 |
| CO-28B | 0.1 | 0.1 | 0.1 | 0.1 | 0.1 | 0.1 | 0.1 |
| Dow Corning 193 | 1.27 | 1.27 | 1.27 | 1.27 | 1.27 | 1.27 | 1.27 |
| Polycat 8 | 0.82 | 0.82 | 0.82 | 0.82 | 0.82 | 0.82 | 0.00 |
| Pel-Cat 9540-A | 0.51 | 0.51 | 0.51 | 0.51 | 0.51 | 0.51 | 0.00 |
| Solstice LBA | 10.18 | 10.18 | 10.18 | 10.18 | 10.18 | 10.18 | 10.17 |
| Total Water | 1.86 | 1.86 | 1.86 | 1.86 | 1.86 | 1.86 | 1.86 |
| Total B Side | 100 | 100 | 100 | 100 | 100 | 100 | 98.67 |

For the following Table 5: Polyol B side formulations for Examples 14-20, the materials and amounts are as follows.

Terol 250 is an aromatic polyester polyol commercially available from Huntsman Corporation. Jeffol R-470X is a Mannich polyol commercially available from Huntsman Corporation. Poly-G 74-376 is a sucrose initiated polyether polyol made with ethylene oxide and propylene oxide commercially available from Monument Chemical.

Polycat 8 is a small molecule amine catalyst commercially available from Air Products and Chemicals, Inc. Pelcat 9540-A is a potassium salt of octanoic acid catalyst commercially available from Ele Corporation.

Diluent DBE esters are a mixture of dibasic esters of the methyl and ethyl esters of adipic, succinic, and glutaric acids Table 5 displays the different formulation variants in using an alkoxylated-triazine-arylhydroxy-aldehyde condensate prepared from Example 1 with Example 16 representing a control formulation without alkoxylated triazine-arylhydroxy-aldehyde condensate. The resulting polyurethane foam reactivity properties are shown in Table 6. Methods for measuring the reactivity in Table 6 were done in accordance with ASTM D7487-13e1. Examples 15, 18, and 20 are free of a Mannich (base) polyol. Example 20 is free of catalysts.

The resulting polyurethane foam reactivity properties are shown in Table 6. Methods for measuring the reactivity in Table 6: Reactivity Of Polyurethane Foam Examples were done in accordance with ASTM D7487-13e1.

TABLE 6

| Foam Property | Ex. 14 | Ex. 15 | Ex. 16 | Ex. 17 | Ex. 18 | Ex. 19 | Ex. 20 |
|---|---|---|---|---|---|---|---|
| Cream Time, s | 10 | 10 | 11 | 8 | 7 | 9 | 17 |
| Gel Time, s | 25 | 21 | 29 | 18 | 13 | 22 | 42 |

TABLE 6-continued

| Foam Property | Ex. 14 | Ex. 15 | Ex. 16 | Ex. 17 | Ex. 18 | Ex. 19 | Ex. 20 |
|---|---|---|---|---|---|---|---|
| Rise Time, s | 36 | 30 | 50 | 24 | 19 | 34 | 52 |
| Tack-free Time, s | 38 | 35 | 54 | 27 | 23 | 38 | 56 |

Reactivity of a foam formulation is evaluated based on the time it takes to achieve the cream, gel, rise and tack-free states. Lesser the time it takes to achieve these states, faster is the reactivity of the formulation. From Table 6, Example 18 that contains the maximum concentration of alkoxylated triazine-arylhydroxy-aldehyde condensate exhibited the highest reactivity of all the polyurethane foams produced and is significantly faster than Example 16, which is the control. Examples 14 and 18 are direct comparison of reactivity between Mannich polyol against alkoxylated triazine-arylhydroxy-aldehyde condensate.

It is clear that the alkoxylated triazine-arylhydroxy-aldehyde condensate is significantly more reactive than Mannich polyol. In addition, Examples 16, 19, 15 and 18 illustrate the effect of increasing the concentration of alkoxylated triazine-arylhydroxy-aldehyde condensate. As the concentration of the alkoxylated triazine-arylhydroxy-aldehyde condensate increase from 0% to 10% to 15% to 30% respectively in these examples, the reactivity also increase consistently as shown by decrease in cream, gel, rise and tack-free times.

Thus, the data in Table 5 demonstrates the significantly higher reactivity of alkoxylated triazine-arylhydroxy-aldehyde condensate compared to the reference polyols. The table also shows that use of the novel polyol of the said invention can minimize or allow the formulation to be free of the use of Mannich base poylols or small molecule amine catalysts that can cause a myriad of health problems for humans including Glaucopsia and respiratory irritation Further, due to the high functionality and aromaticity of the alkoxylated triazine-arylhydroxy-aldehyde condensates a formulator could likely develop a polyurethane composition that has no catalyst and no additional polyols, which could simplify complex formulations and minimize errors in producing B side formulations. An example of this formulation could be alkoxylated triazine arylhydroxy-aldehyde condensate, a suitable surfactant, a suitable blowing agent, and a suitable fire retardant.

Data for fire retardant properties is provided in Table 7: Burn Characteristics of Examples 14-19 below.

TABLE 7

| Properties | Ex. 14 | Ex. 15 | Ex. 16 | Ex. 17 | Ex. 18 | Ex. 19 |
|---|---|---|---|---|---|---|
| Horizontal Burn Rate, mm/min | 175 ± 11 | 142 ± 9 | 238 ± 16 | 104 ± 6 | Self-extinguished | 187 ± 16 |
| Mass retention, % | 48.2 ± 2.8 | 50.8 ± 4.4 | 45 ± 4.2 | 51 ± 3.6 | 86.8 ± 6.5 | 50.8 ± 4.7 |

The burn rate and weight retention after burning were measured using in-house modified ASTM D 4986 flammability test. In the in-house test, Bernzomatic torch TS4000 was used. This flammability test is relatively simple and designed for relative comparison between different foam types. Lower the mm/rate and higher the mass retention indicate better reaction to fire or improved fire resistance.

Table 7 shows the effect of polyol on the foam's reaction to fire. As the concentration of the alkoxylated triazine-arylhydroxy-aldehyde condensate increase from 0% to 10% to 15% to 30% respectively in Examples 16, 19, 15 and 18 respectively, the burn rate decrease consistently and at a maximum concentration of 30% in the absence of both—the sugar-based polyether and Mannich polyol, the foam displayed self-extinguishing property. The higher mass retention of the remnants is also a direct consequence of improved flame resistance. Example 16, the control sample had a mass retention of 45%; Example 18 with 30% of alkoxylated triazine-arylhydroxy-aldehyde condensate had a mass retention of 87%.

In addition to allowing for simplified B side formulations it is further anticipated that the alkoxylated triazine arylhydroxy-aldehyde condensates will have better miscibility with aromatic isocyanates and blowing agents such as pentanes and their associate isomers, hydroxyl fluorinated olefins, hydroxyl fluorinated hydrocarbons, and other halogenated blowing agents when compared to common polyols such as sucrose polyether polyols or other polyethers of sufficient hydrophilicity, Mannich polyols, aromatic polyester polyols, ethylene diamine polyethers polyols.

Finally, the alkoxylated triazine-arylhydroxy-aldehyde condensates when reacted with an isocyanate have demonstrated relatively high onsets of thermal degradation and due to the nitrogen content present in the polyol could yield a synergistic effect with phosphorous containing compounds, which could significantly improve the fire retardant properties of a typical polyurethane foam or associated article.

While the present invention has been described and illustrated by reference to particular embodiments, those of ordinary skill in the art will appreciate that the invention lends itself to variations not necessarily illustrated herein.

What is claimed is:

1. A condensation product of a reaction mixture comprising: a 1,3,5-triazine-arylhydroxy-aldehyde condensate and alkoxylation by an alkoxylation agent comprising: an alkylene oxide; and an optional alkylene carbonate; and an optional catalyst, wherein the alkylene oxide is an epoxy functional compound and wherein the 1,3,5-triazine moiety of the 1,3,5-triazine-arylhydroxy-aldehyde condensate comprises at least one optionally substituted amino group.

2. The condensation product of claim 1, wherein the at least one alkylene oxide comprises a compound selected from the group consisting of ethylene oxide, propylene oxide, butylene oxide, and combinations thereof.

3. The condensation product of claim 1, wherein the optional alkylene carbonate comprises a compound selected from the group consisting of ethylene carbonate, propylene carbonate, butylene carbonate, and combinations thereof.

4. The condensation product of claim 1, wherein the optional catalyst comprises a compound selected from the group consisting of a metal hydroxide, a metal carbonate, a tertiary amine, a phosphine, a transition metal base, a metal phosphate, an organic acid, and combinations thereof.

5. The condensation product of claim 1, wherein each reactive site of the 1,3,5-triazine-arylhydroxy-aldehyde condensate possesses from 1 mole to 20 moles of an alkoxylation agent.

6. The condensation product of claim 1, wherein the condensation product comprises an alkoxylated triazine-arylhydroxy-aldehyde condensate having a structure of:

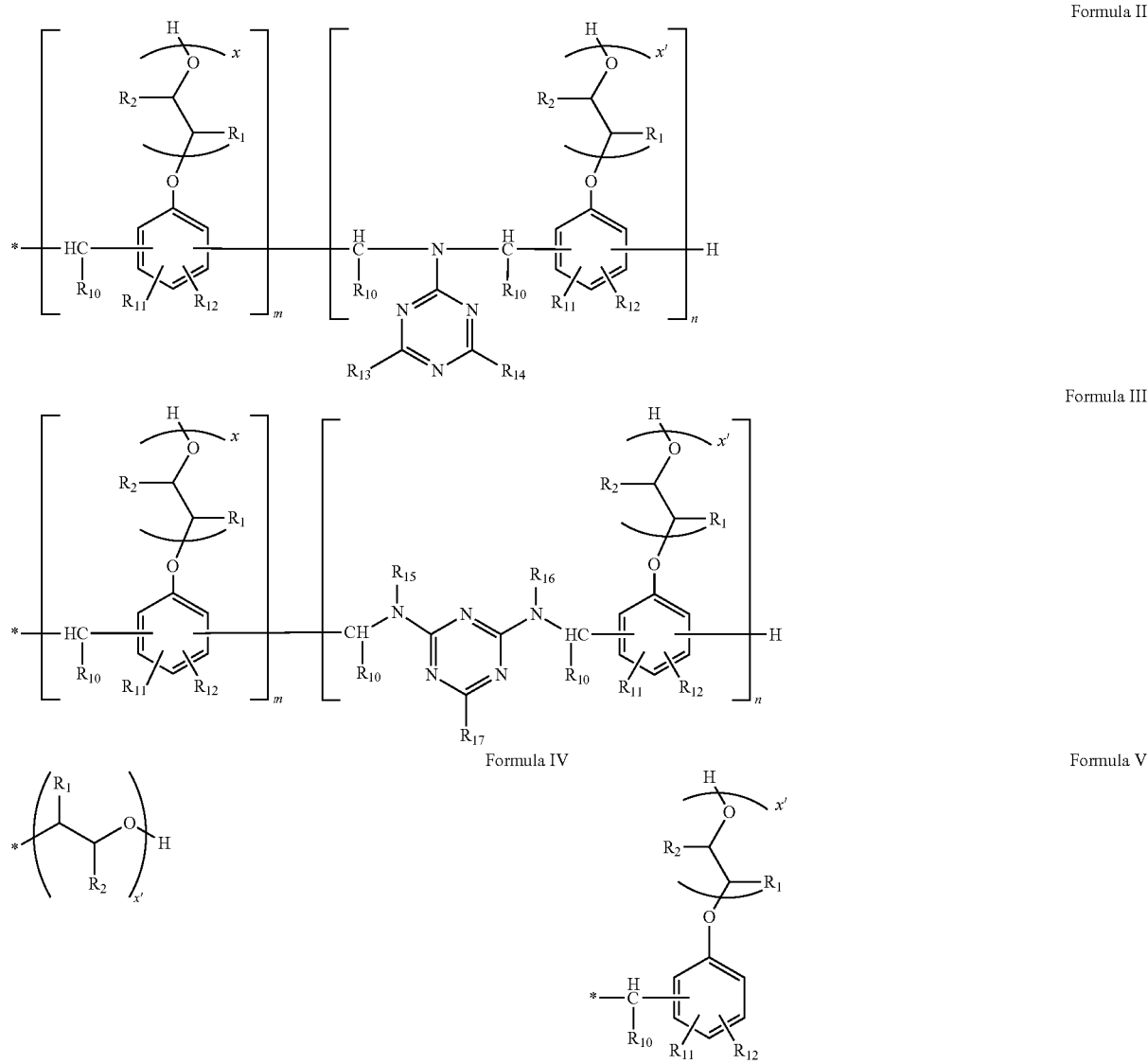

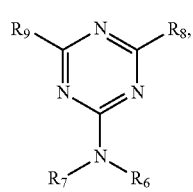

wherein $R_6$ is Formula II or Formula III, and wherein $R_7$ is a hydrogen atom, Formula II, or Formula IV;

wherein $R_8$ and $R_9$ are each independently a hydrogen atom, an alkyl group with 1 to 10 carbon atoms, a vinyl group, a phenyl group, a hydroxyphenyl group, —NH(Formula IV), —N(Formula IV)$_2$, —NH(Formula II), —N(Formula II)(Formula IV), —N(Formula II)$_2$, —NH(Formula III), —N(Formula III)(Formula IV), —N(Formula III)$_2$, NH(Formula V), —N(Formula IV)(Formula V), —N(Formula V)$_2$, or NH$_2$;

wherein $R_1$ and $R_2$ are each independently a hydrogen atom, an alkyl group having 1 to 4 carbon atoms, a vinyl group, or an alkyl group with 1 to 4 carbon atoms containing a hydroxyl group;

wherein $R_{10}$ is a hydrogen atom, an alkyl group with 1 to 10 carbon atoms, an alkyl group with 1 to 10 carbon atoms containing a hydroxyl group, a phenyl group, a vinyl group, a propenyl group, a hydroxyl containing phenyl group, a pyrrole group, or a (uranyl group;

wherein $R_{11}$ and $R_{12}$ are each independently a hydrogen atom, an alkyl group with 1 to 10 carbon atoms, an alkoxy group having 1 to 10 carbon atoms, a phenyl group, a hydroxybenzene group, or an alkyl group with 1 to 10 carbon atoms with at least one carbon substituted with i) a hydroxyl group, ii) a hydroxybenzene group, or iii) a phenyl group;

or wherein $R_{11}$ and $R_{12}$ jointly form a common aromatic ring with or without a hydroxyl group;

wherein $R_{13}$ and $R_{14}$ are each independently a hydrogen atom, an alkyl group with 1 to 10 carbon atoms, a vinyl group, a phenyl group, a hydroxyphenyl group, —NH(Formula IV), —N(Formula IV)$_2$, —NH(Formula V), —N((Formula IV)(Formula V)), —N(Formula V)$_2$, or NH$_2$;

wherein $R_{15}$, $R_{16}$, and $R_{17}$ are each independently a hydrogen atom, an alkyl group with 1 to 10 carbon atoms, a vinyl group, a phenyl group, a hydroxyphenyl group, —NH(Formula IV), —N(Formula IV)$_2$, —NH(Formula V), —N(Formula IV)(Formula V), —N(Formula V)$_2$, or —NH$_2$;

wherein each m is independently from 1 to 10, each n is independently from 0 to 10, wherein each x is independently from 1 to 20, and each x' is independently from 1 to 20 when an alkoxylation agent is an alkylene oxide or wherein each x is independently from 1 to 20, and each x is independently from 1 to 20 with the average of all x and x' is greater than 2 when the alkoxylation agent is a combination of an alkylene oxide and an alkylene carbonate, and wherein monomers depicted by m and n are arranged in any order, combination, or sub-combination.

7. The condensation product of claim 1, wherein the condensation product comprises one or more compounds selected from the group consisting of:

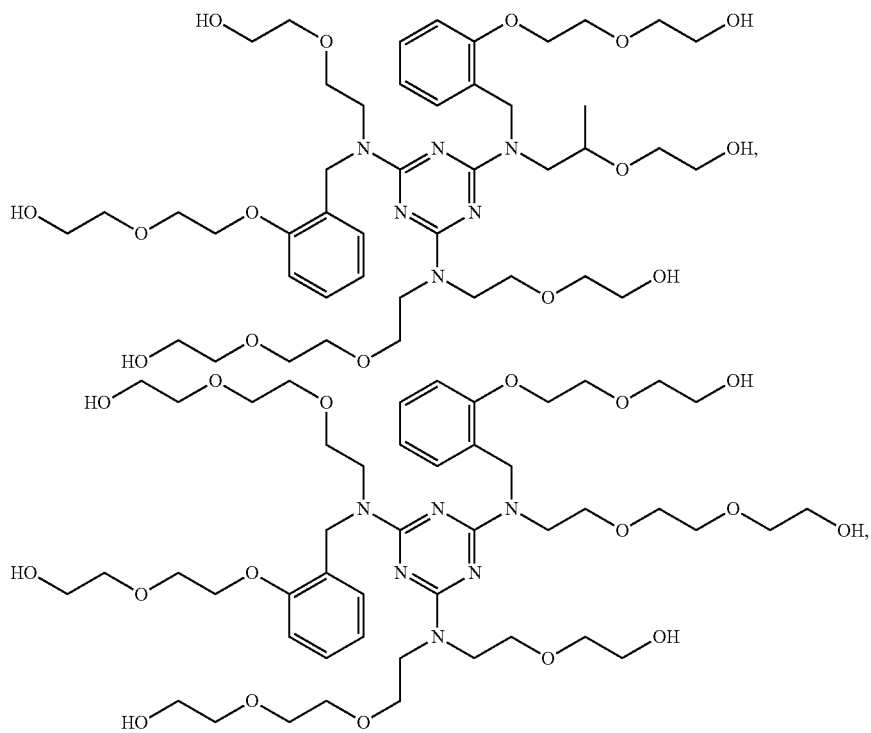

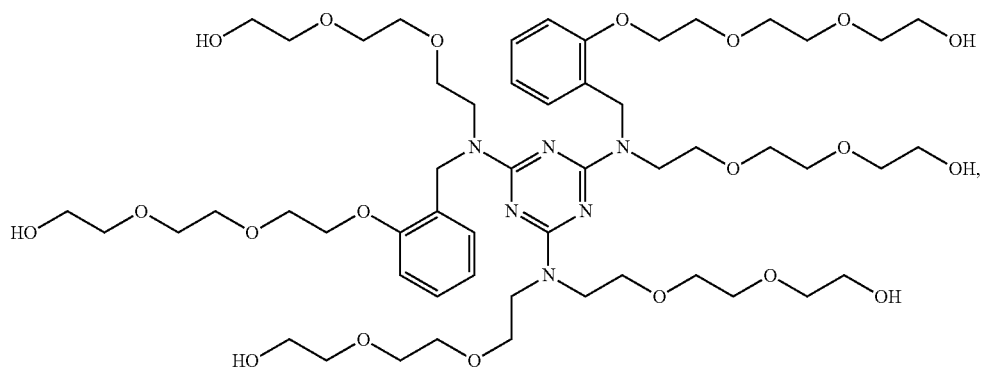

-continued
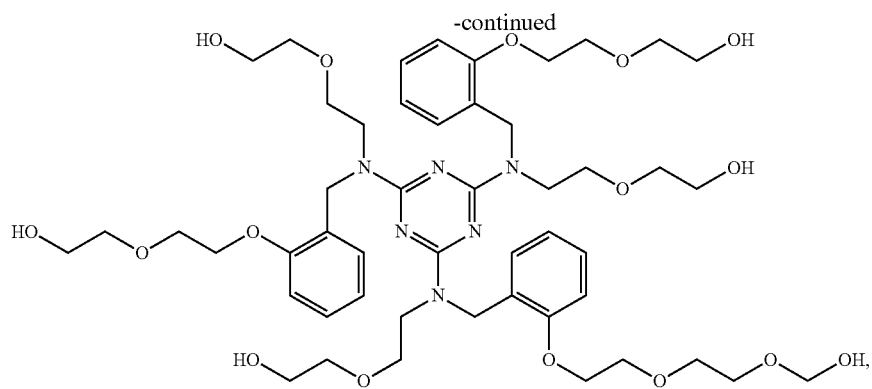
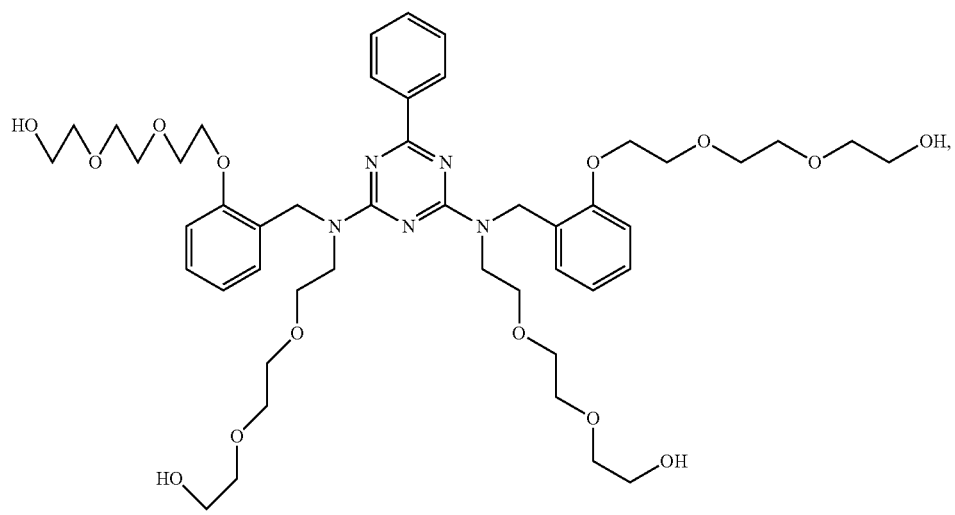
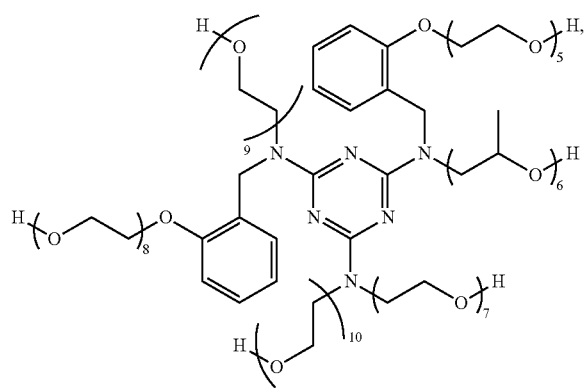

-continued

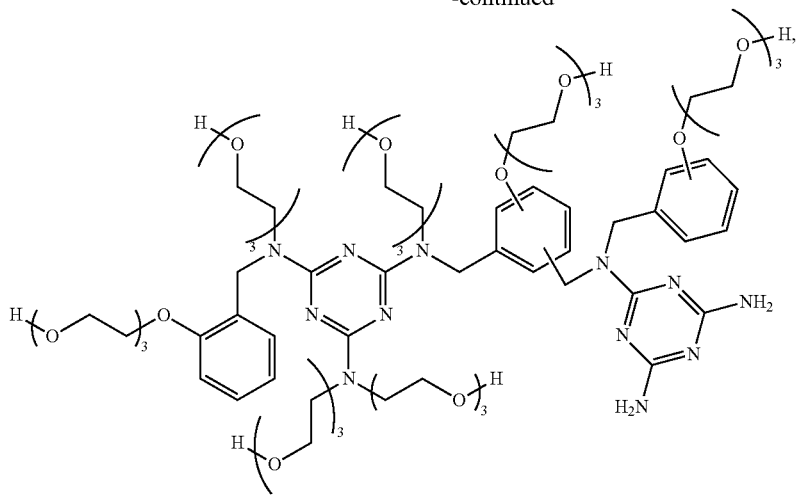

and combinations thereof.

8. The condensation product of claim 1, wherein the condensation product comprises a nitrogen content from about 1 wt. % to 41 wt. %.

9. The condensation product of claim 1, wherein the condensation product comprises an aromatic content from about 1 up to 69 weight percent.

10. An alkoxylated triazine-arylhydroxy-aldehyde condensate compound having a structure of:

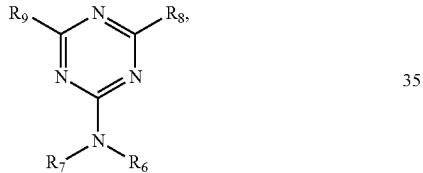

wherein $R_6$ is Formula II or Formula III, and wherein $R_7$ is a hydrogen atom, Formula II, or Formula IV;

wherein $R_8$ and $R_9$ are each independently a hydrogen atom, an alkyl group with 1 to 10 carbon atoms, a vinyl group, a phenyl group, a hydroxyphenyl group, —NH(Formula IV), —N(Formula IV)$_2$, —NH(Formula II), —N(Formula II)(Formula IV), —N(Formula II)$_2$, —NH(Formula III), —N(Formula III)(Formula IV), —N(Formula III)$_2$, NH(Formula V), —N(Formula IV)(Formula V), —N(Formula V)$_2$, or —NH$_2$;

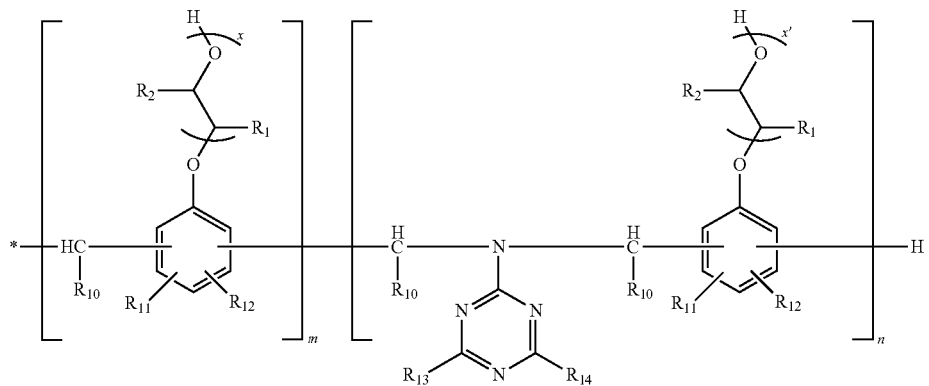

Formula II

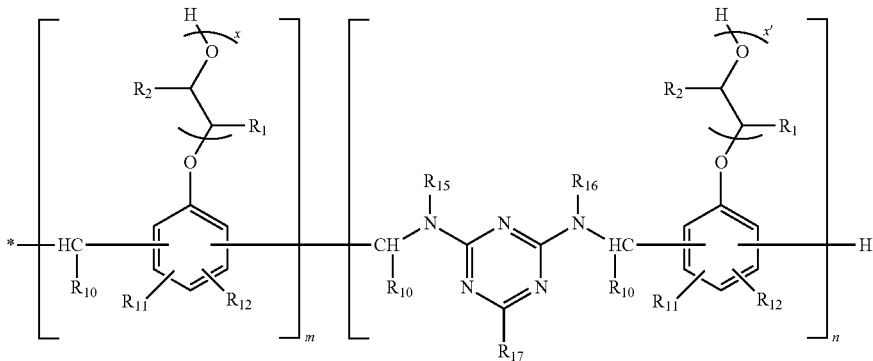

Formula III

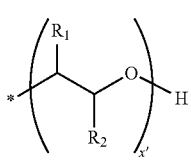

Formula V

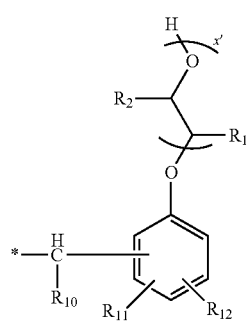

Formula IV wherein $R_1$ and $R_2$ are each independently a hydrogen atom, an alkyl group having 1 to 4 carbon atoms, a vinyl group, or an alkyl group with 1 to 4 carbon atoms containing a hydroxyl group;

wherein $R_{10}$ is a hydrogen atom, an alkyl group with 1 to 10 carbon atoms, an alkyl group with 1 to 10 carbon atoms containing a hydroxyl group, a phenyl group, a vinyl group, a propenyl group, a hydroxyl containing phenyl group, a pyrrole group, or a (uranyl group;

wherein $R_{11}$ and $R_{12}$ are each independently a hydrogen atom, an alkyl group with 1 to 10 carbon atoms, an alkoxy group having 1 to 10 carbon atoms, a phenyl group, a hydroxybenzene group, or an alkyl group with 1 to 10 carbon atoms with at least one carbon substituted with i) a hydroxyl group, ii) a hydroxybenzene group, or iii) a phenyl group;

or wherein $R_{11}$ and $R_{12}$ jointly form a common aromatic ring with or without a hydroxyl group;

wherein $R_{13}$ and $R_{14}$ are each independently a hydrogen atom, an alkyl group with 1 to 10 carbon atoms, a vinyl group, a phenyl group, a hydroxyphenyl group, —NH(Formula IV), —N(Formula IV)$_2$, —NH(Formula V), —N((Formula IV)(Formula V)), —N(Formula V)$_2$, or —NH$_2$;

wherein $R_{15}$, $R_{16}$, and $R_{17}$ are each independently a hydrogen atom, an alkyl group with 1 to 10 carbon atoms, a vinyl group, a phenyl group, a hydroxyphenyl group, —NH(Formula IV), —N(Formula IV)$_2$, —NH(Formula V), —N(Formula IV)(Formula V), —N(Formula V)$_2$, or —NH$_2$;

wherein each m is independently from 1 to 10, each n is independently from 0 to 10, wherein each x is independently from 1 to 20, and each x' is independently from 1 to 20 when an alkoxylation agent is an alkylene oxide or wherein each x is independently from 1 to 20, and each x' is independently from 1 to 20 with the average of all x and x' is greater than 2 when the alkoxylation agent is a combination of an alkylene oxide and an alkylene carbonate, and wherein monomers depicted by m and n are arranged in any order, combination, or sub-combination.

11. The compound of claim 10, wherein the alkoxylated triazine-arylhydroxy-aldehyde condensate composition comprises one or more compounds selected from the group consisting of having a structure of:

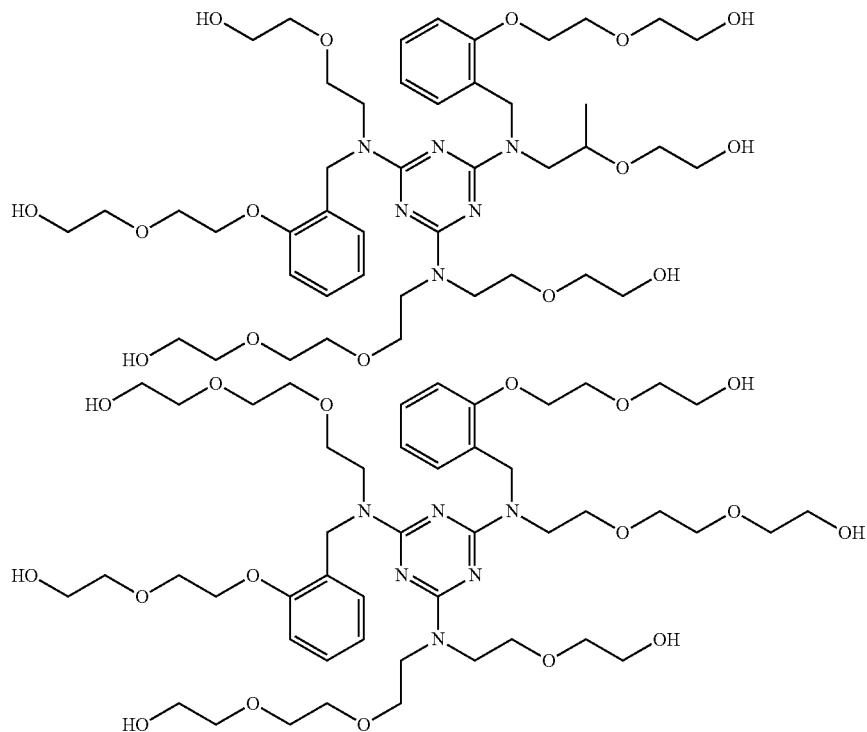
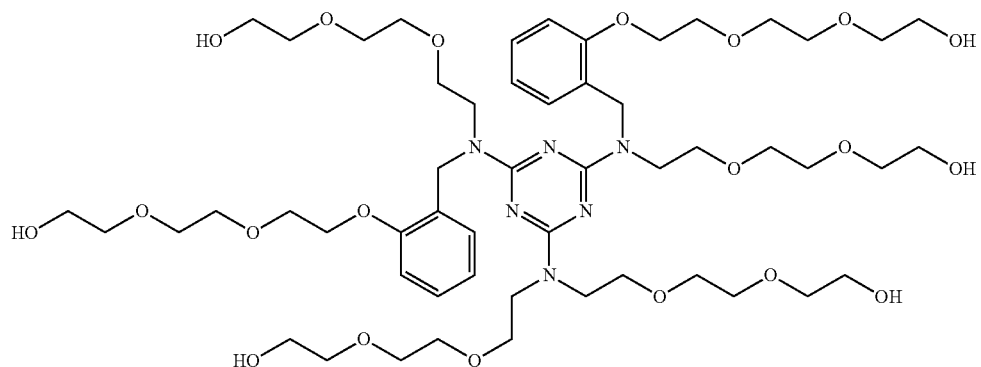
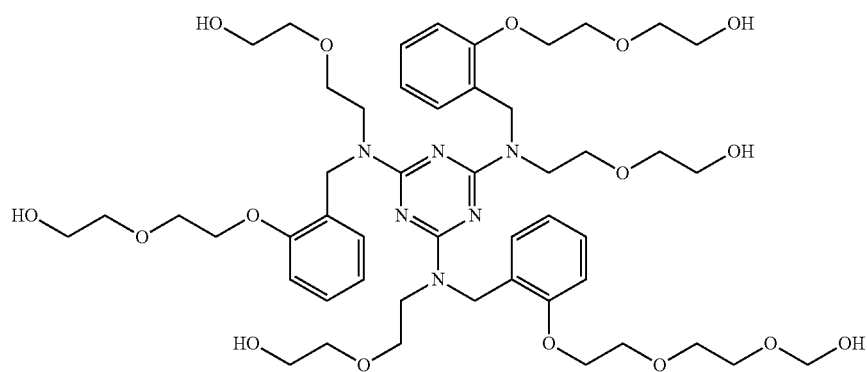

-continued

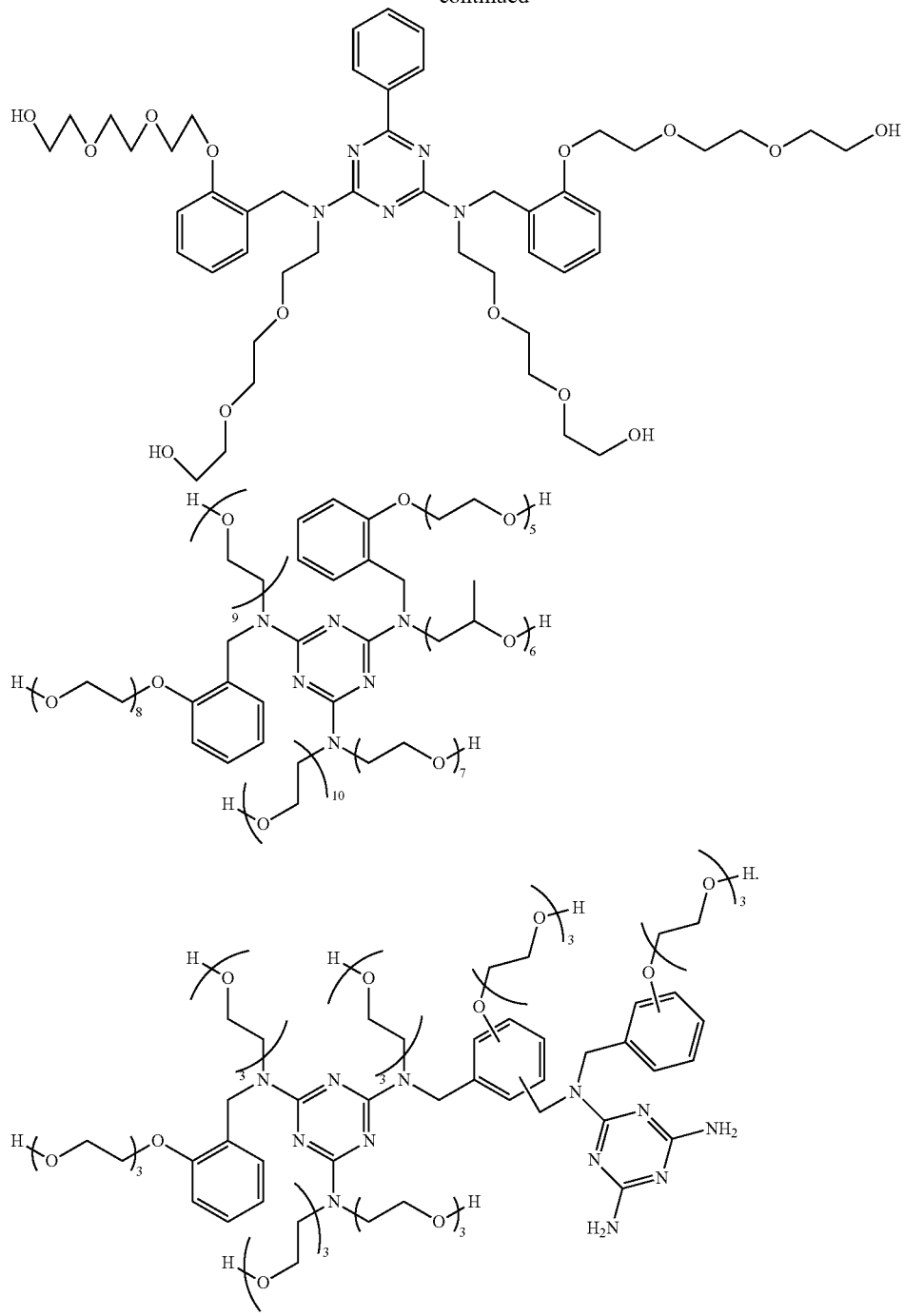

12. The compound of claim 10, wherein the alkoxylated-triazine-arylhydroxy-aldehyde condensate composition further comprises a rheology modifier in polyurethane cross-linking applications.

13. A process comprising: alkoxylating a 1, 3, 5-triazine-arylhydroxy-aldehyde condensate by reacting with at least one alkylene oxide, alone or in combination with an alkylene carbonate, optionally in the presence of a catalyst; and forming an alkoxylated triazine-arylhydroxy-aldehyde condensate composition, wherein the alkylene oxide is an epoxy functional compound and wherein the 1,3,5-triazine moiety of the 1,3,5-triazine-arylhydroxy-aldehyde condensate comprises at least one optionally substituted amino group.

14. The process of claim 13, wherein the alkylene oxide is selected from the group consisting of ethylene oxide, propylene oxide, butylene oxide and mixtures thereof and in any order.

15. The process of claim 13, wherein the alkylene oxide is a compound selected from the group consisting of ethylene oxide, propylene oxide, butylene oxide and mixtures thereof, and the alkylene carbonate is a compound selected from the group consisting of ethylene carbonate, propylene carbonate and mixtures thereof.

16. The process of claim 13, wherein manufacturing 1,3,5-triazine-arylhydroxy-aldehyde condensate and forming the alkoxylated 1,3,5-triazine-arylhydroxy-aldehyde condensate composition are carried out in the same reactor.

17. The process of claim 13, wherein manufacturing triazine-arylhydroxy-aldehyde condensate and forming the alkoxylated 1,3,5-triazine-arylhydroxy-aldehyde condensate composition are carried out in a continuous, semi-continuous, semi-continuous to batch, or batch type reactor.

18. The condensation product of claim 1, wherein the at least one alkylene oxide comprises a compound selected from the group consisting of ethylene oxide, propylene oxide, glycidol, styrene oxide, epichlorohydrin, butylene oxide, isobutyleneoxide, cyclohexane oxide, 2,3-epoxyhexane, allyl glycidyl ether, methyl glycidyl ether, butyl glycidyl sulfide, glycidyl methyl sulfone, glycidyl methacrylate, glycidyl allyl phthalate, and combinations thereof.

19. A condensation product of a reaction mixture comprising: a 1,2,3-triazine-arylhydroxy-aldehyde condensate and alkoxylation by an alkoxylation agent comprising: an alkylene oxide; and an optional alkylene carbonate; and an optional catalyst, wherein the alkylene oxide is an epoxy functional compound and wherein the 1,2,3-triazine moiety of the 1,2,3-triazine-arylhydroxy-aldehyde condensate comprises at least one optionally substituted amino group.

20. A condensation product of a reaction mixture comprising: a 1,2,4-triazine-arylhydroxy-aldehyde condensate and alkoxylation by an alkoxylation agent comprising: an alkylene oxide; and an optional alkylene carbonate; and an optional catalyst, wherein the alkylene oxide is an epoxy functional compound and wherein the 1,2,4-triazine moiety of the 1,2,4-triazine-arylhydroxy-aldehyde condensate comprises at least one optionally substituted amino group.

* * * * *